US012274805B1

(12) United States Patent
Simmons et al.

(10) Patent No.: US 12,274,805 B1
(45) Date of Patent: Apr. 15, 2025

(54) MICROFOAMING AQUEOUS OZONE DISINFECTION

(71) Applicant: BioSure North America LLC, Fair Oaks Ranch, TX (US)

(72) Inventors: Darren Simmons, Fair Oaks Ranch, TX (US); Ivor J. J. Longo, Atlanta, TX (US); Wayne Simmons, Adkins, TX (US); James R. Muscott, Summerville, SC (US); H. Brock Kolls, Alpharetta, GA (US)

(73) Assignee: BioSure North America LLC, Fair Oaks Ranch, TX (US)

( * ) Notice: Subject to any disclaimer, the term of this patent is extended or adjusted under 35 U.S.C. 154(b) by 0 days.

(21) Appl. No.: 18/782,055

(22) Filed: Jul. 24, 2024

Related U.S. Application Data

(63) Continuation-in-part of application No. 18/760,262, filed on Jul. 1, 2024, now Pat. No. 12,171,914, and a continuation-in-part of application No. 18/760,274, filed on Jul. 1, 2024, now Pat. No. 12,151,055, and a continuation-in-part of application No. 18/646,394,
(Continued)

(51) Int. Cl.
| | |
|---|---|
| *A61L 2/18* | (2006.01) |
| *A61C 17/02* | (2006.01) |
| *A61L 2/00* | (2006.01) |
| *A61L 2/26* | (2006.01) |
| *A61L 101/02* | (2006.01) |
| *C01B 13/10* | (2006.01) |
| *C25B 1/13* | (2006.01) |

(52) U.S. Cl.
CPC .............. *A61L 2/183* (2013.01); *A61C 17/02* (2013.01); *A61L 2/0088* (2013.01); *A61L 2/26* (2013.01); *C01B 13/10* (2013.01); *C25B 1/13* (2013.01); *A61L 2101/02* (2020.08); *A61L 2202/11* (2013.01); *A61L 2202/14* (2013.01); *A61L 2202/15* (2013.01); *A61L 2202/24* (2013.01)

(58) Field of Classification Search
CPC .......... A61L 2/183; A61L 2/0088; A61L 2/26; A61C 17/02; C01B 13/10; C25B 1/13
See application file for complete search history.

(56) References Cited

U.S. PATENT DOCUMENTS 6,458,257 B1 * 10/2002 Andrews ............... C02F 1/4672
204/266

FOREIGN PATENT DOCUMENTS

| WO | WO-9742924 A1 * | 11/1997 | .......... A61C 1/0076 |
| WO | WO-0237965 A2 * | 5/2002 | ............. A01N 59/00 |

* cited by examiner

Primary Examiner — Sean E Conley
(74) Attorney, Agent, or Firm — H. Brock Kolls

(57) ABSTRACT

The present invention relates to a microfoaming aqueous ozone disinfection system that comprises an aqueous ozone generator that receives water, a microfoaming agent, and an electrochemical generator that comprises an ion exchange material. The electrochemical generator is integrated into the aqueous ozone generator. The electrochemical generator receives the water and generates from the water an ozonated concentrate liquid. The microfoaming aqueous ozone disinfection system also comprises a mixer that blends the microfoaming agent with the ozonated concentrate liquid creating a microfoaming ozonated liquid that is dispensed for use in disinfecting one or more surfaces. Replaceable cartridges can include the microfoaming agent. The system can data communicate with remote data processing resources, including communicating when it is time to replace the cartridge.

20 Claims, 14 Drawing Sheets

Related U.S. Application Data filed on Apr. 25, 2024, and a continuation-in-part of application No. 18/628,678, filed on Apr. 6, 2024, now Pat. No. 12,089,592, and a continuation-in-part of application No. 18/628,680, filed on Apr. 6, 2024, now Pat. No. 12,137,699, and a continuation-in-part of application No. 18/428,523, filed on Jan. 31, 2024, now Pat. No. 12,070,051.

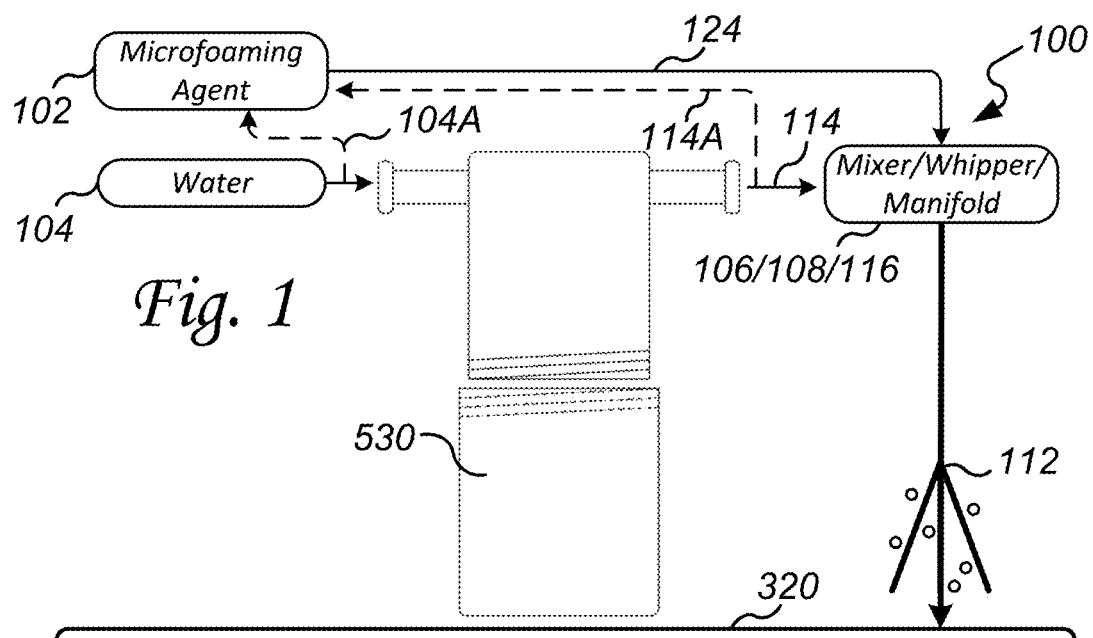
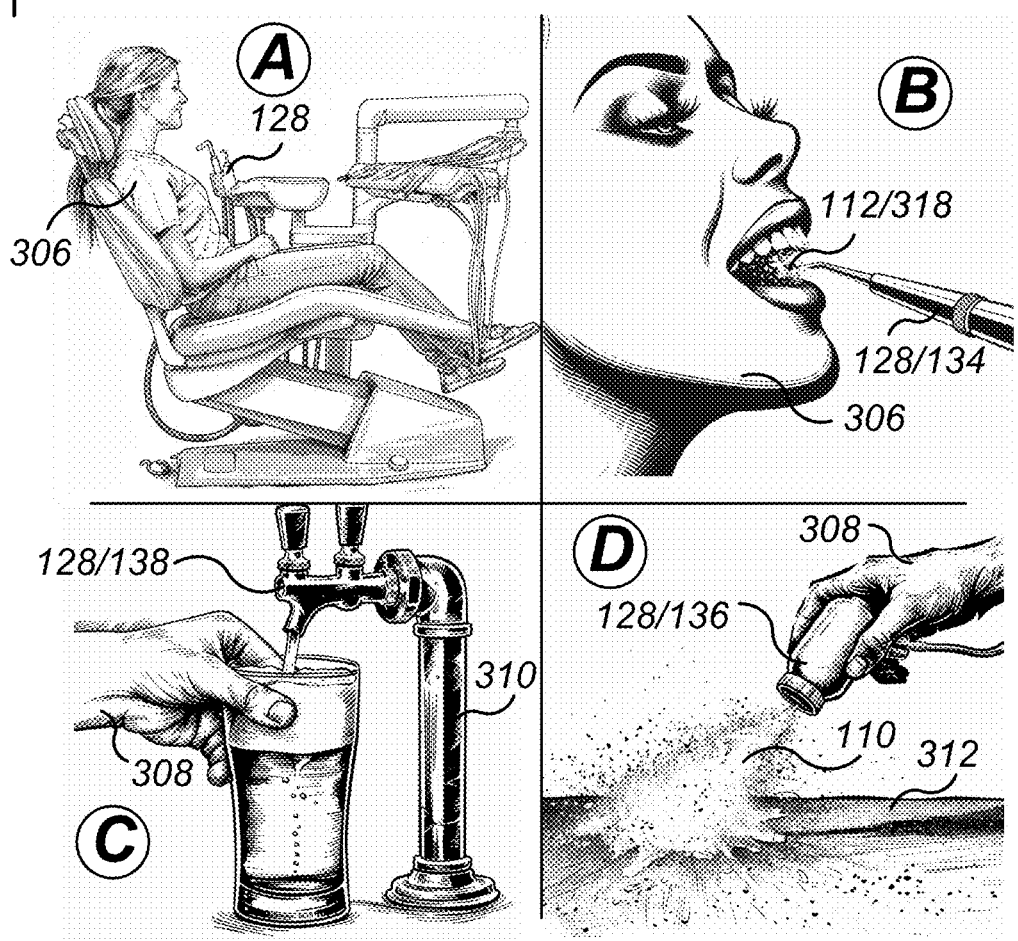
Fig. 1

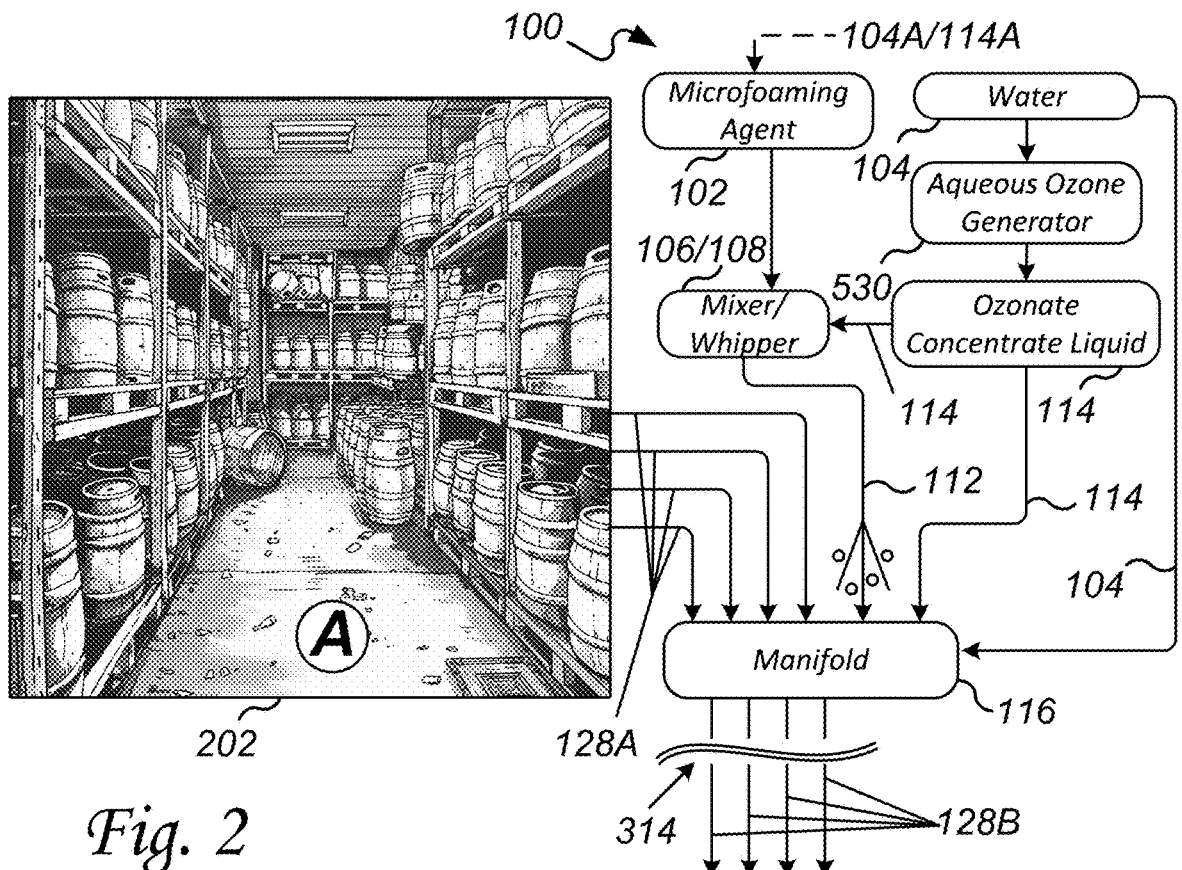
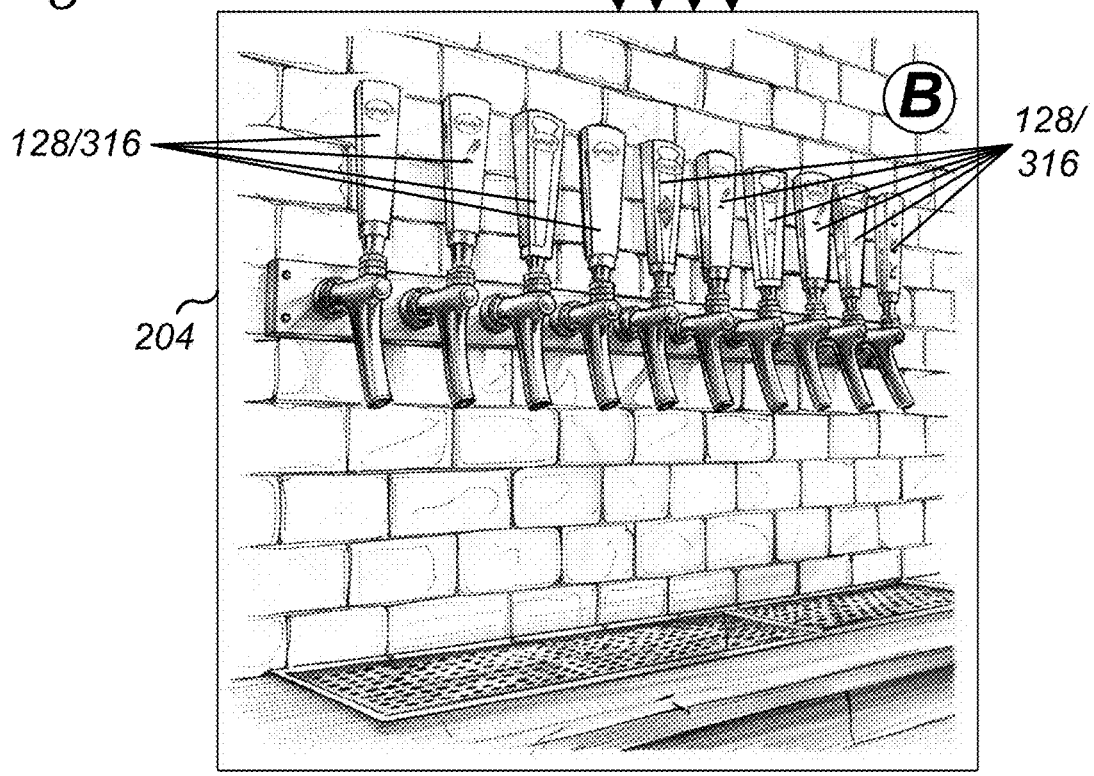
Fig. 2

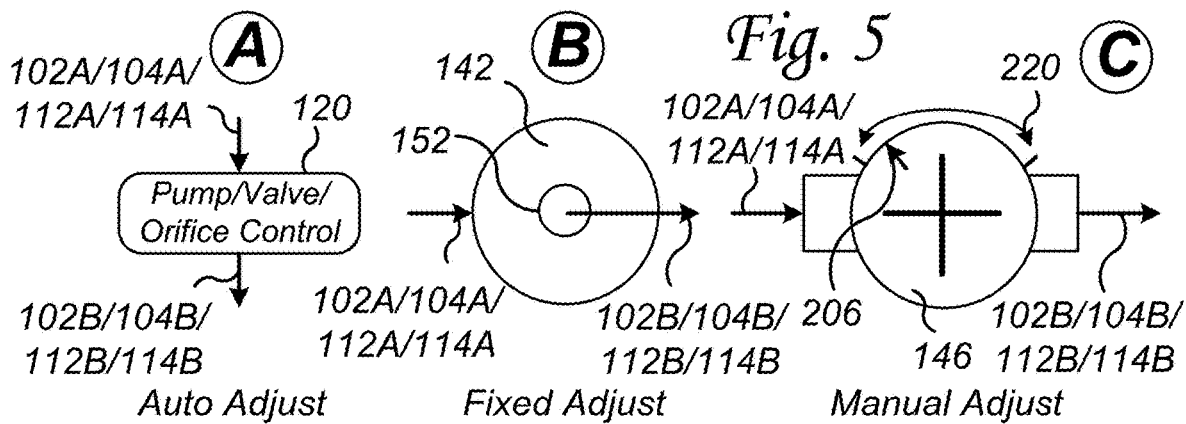
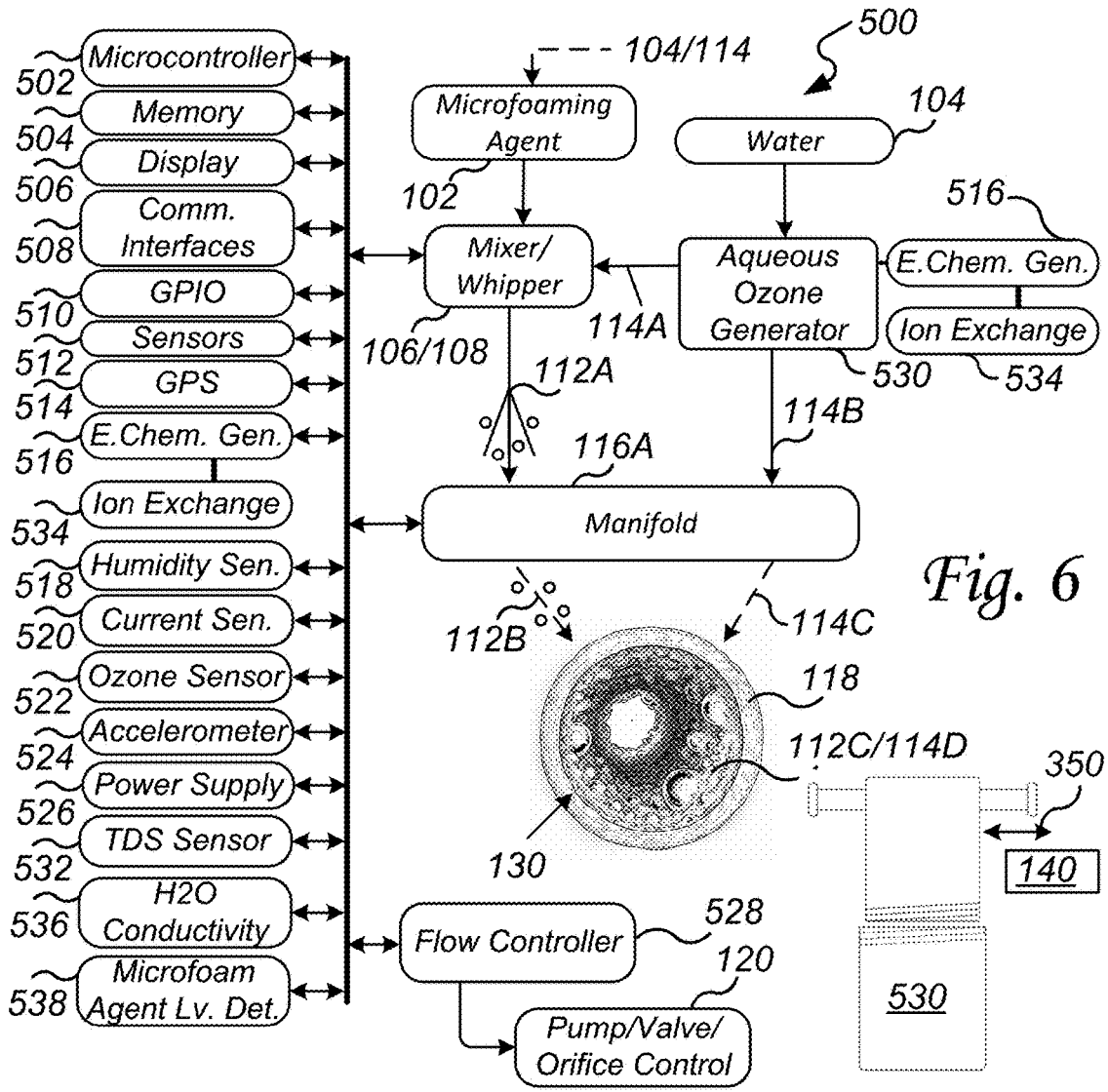

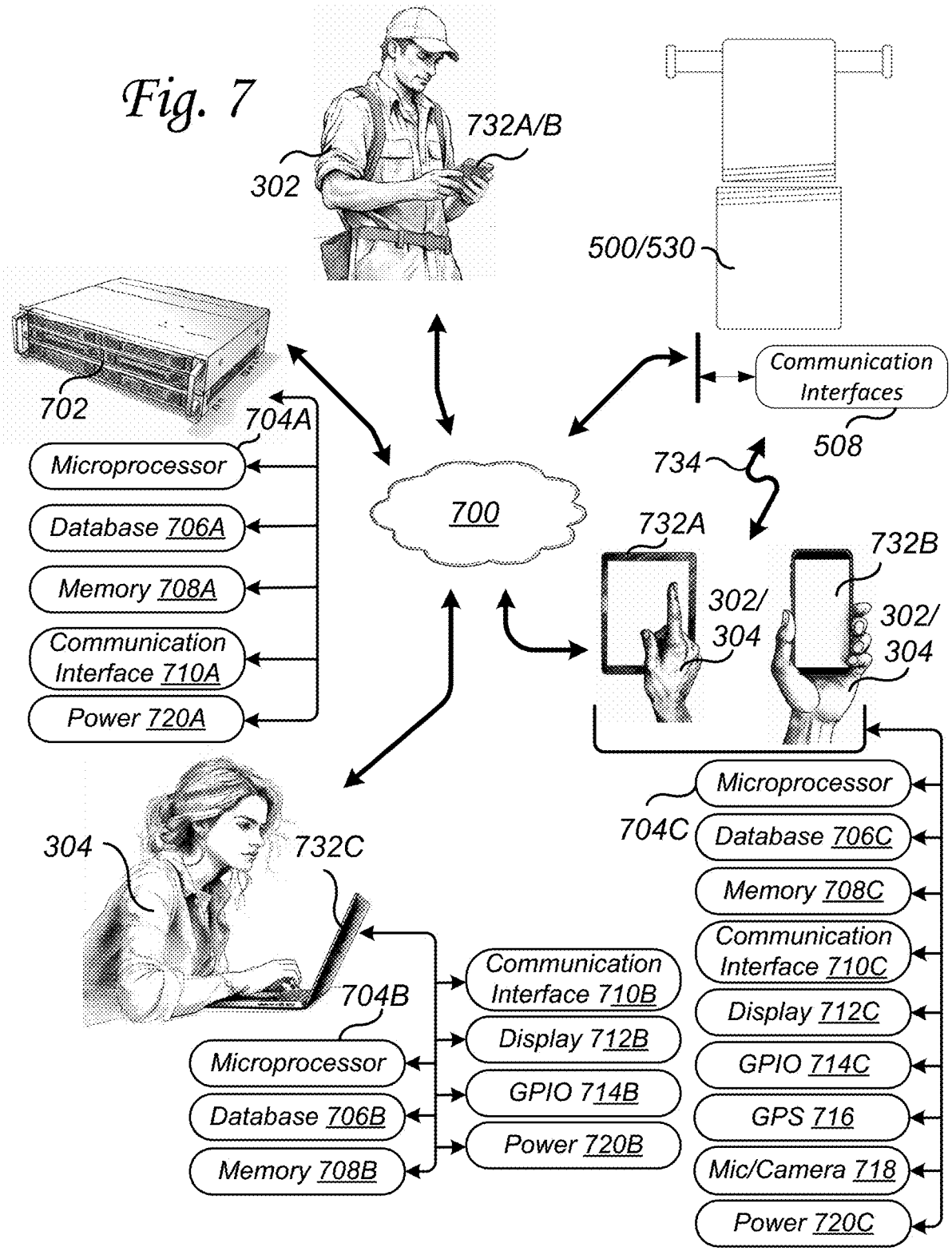

MICROFOAMING AQUEOUS OZONE DISINFECTION

CROSS-REFERENCE TO RELATED APPLICATIONS

This application contains subject matter which is related to the subject matter of the following co-pending applications. The below-listed applications are hereby incorporated herein by reference in its entirety:

This U.S. non-provisional application is a continuation in part of a U.S. non-provisional application Ser. No. 18/760,262, inventor Gavin Hsu et al., entitled "DEODORIZING AIR USING AQUEOUS OZONE AS A CATALYST", filed Jul. 1, 2024, and a continuation in part of U.S. non-provisional application Ser. No. 18/760,274, inventor Gavin Hsu et al., entitled "DEODORIZING AIR USING AQUEOUS OZONE AS A CATALYST", filed Jul. 1, 2024;

This U.S. non-provisional application is a continuation in part of a U.S. non-provisional application Ser. No. 18/628,678, inventor Darren Simmons et al., entitled "POST-HARVEST LETTUCE TREATMENT METHODS", filed Apr. 6, 2024, and a continuation in part of U.S. non-provisional application Ser. No. 18/628,680, inventor Darren Simmons et al., entitled "FOOD PREPARATION DISINFECTION TREATMENT METHODS", filed Apr. 6, 2024, and a continuation in part of U.S. non-provisional application Ser. No. 18/428,523, inventor Darren Simmons et al., entitled "AQUEOUS OZONE DISINFECTION SYSTEM", filed Jan. 31, 2024; and This U.S. non-provisional application is a continuation in part of a U.S. non-provisional application Ser. No. 18/646,394, inventor Darren Simmons et al., entitled "AQUEOUS OZONE FLOOR DISINFECTION SYSTEM", filed Apr. 25, 2024, which is a continuation in part of a U.S. non-provisional application Ser. No. 18/528,194, inventor Darren Simmons et al., entitled "AQUEOUS OZONE FLOOR DISINFECTION SYSTEM", filed Dec. 4, 2023, now patent No. 12,036,331, and a continuation in part of a U.S. non-provisional application Ser. No. 18/528,162, inventor Darren Simmons et al., entitled "AQUEOUS OZONE FLOOR DISINFECTION SYSTEM", filed Dec. 4, 2023, now U.S. Pat. No. 11,975,118.

TECHNICAL FIELD OF THE INVENTION

This invention relates to microfoaming aqueous ozone disinfection systems and methods of use including fluid transmission line disinfection in food and beverage line and surface disinfection applications, dental water line and surface disinfection applications, and other line and surface disinfection, as well as dental patient oral cavity microfoaming ozone rinse applications and other surface disinfection applications.

BACKGROUND OF THE INVENTION

Before our invention, caustic chemicals were commonly used to clean and disinfect tubing and piping that carry food and beverage products. In this regard, these types of fluid handling tubes can see biofilms and other contaminates build up on the interior walls. Such biofilm buildup can affect the flow rate, and taste of the food or beverage running through the tubes, and even make people sick. This is a shortcoming in the food and beverage markets in areas such as beer lines, yogurt lines and equipment, soda/syrup lines, and other food and beverage tubing or piping lines, as well as in dental water lines where medical instruments are washed, and patients' mouths sprayed with water to rinse during dental procedures among other areas of dental waterline usage.

With regards to dental water lines, a shortcoming is that often the patient's mouth rinse occurs when gums and other mouth areas are most susceptible to infection, and thus biofilm and contaminated laced rinse water lines can make patients very sick and infect dental and periodontal wound areas.

A shortcoming, when trying to remove biofilm from tubes and pipes is that there are limited ways to rub or agitate the biofilm that buildups thus often preventing through disinfection of the tubes or pipes, in short scraping biofilm from the sides of tubes and pipes is impractical due to inaccessibility, particularly in long runs of tubes and pipes and thus disinfection by passing caustic or other liquid over the biofilm might not be sufficient for a total cleaning and disinfection.

The present invention addresses these and other shortcomings by providing microfoaming aqueous ozone disinfection and other advantages. For these reasons and shortcomings as well as other reasons and shortcomings there is a long-felt need that gives rise to the present invention.

SUMMARY OF THE INVENTION

The shortcomings of the prior art are overcome and additional advantages are provided through the provision of a microfoaming aqueous ozone disinfection system that comprises an aqueous ozone generator that receives water, a microfoaming agent, and an electrochemical generator that comprises an ion exchange material. The electrochemical generator is integrated into the aqueous ozone generator. The electrochemical generator receives the water and generates from the water an ozonated concentrate liquid. The microfoaming aqueous ozone disinfection system also comprises a mixer that blends the microfoaming agent with the ozonated concentrate liquid creating a microfoaming ozonated liquid that is dispensed for use in disinfecting one or more surfaces.

Additional shortcomings of the prior art are overcome and additional advantages are provided through the provision of a microfoaming aqueous ozone disinfection system that comprises an aqueous ozone generator that receives water, a microfoaming agent, a cartridge that inserts into fluid communication with the aqueous ozone generator, in a removable manner. The cartridge comprises the microfoaming agent. The microfoaming aqueous ozone disinfection system also comprises an electrochemical generator that comprises an ion exchange material. The electrochemical generator is integrated into the aqueous ozone generator. The electrochemical generator receives the water and generates from the water an ozonated concentrate liquid, and a mixer blends the microfoaming agent with the ozonated concentrate liquid, creating a microfoaming ozonated liquid that is dispensed for use in disinfecting one or more surfaces.

Additional shortcomings of the prior art are overcome and additional advantages are provided through the provision of a microfoaming aqueous ozone disinfection system that comprises an aqueous ozone generator that receives water, a microfoaming agent, and an electrochemical generator that comprises an ion exchange material. The electrochemical generator is integrated into the aqueous ozone generator. The electrochemical generator receives the water and generates from the water an ozonated concentrate liquid.

The microfoaming aqueous ozone disinfection system also comprises a mixer that blends the microfoaming agent with the ozonated concentrate liquid, creating a microfoaming ozonated liquid that is dispensed for use in disinfecting one or more surfaces, and a control system that comprises a microcontroller, a memory, a communication interface, and a microfoaming agent level detector.

In operation, the microcontroller is operationally related to the memory, the communication interface, and the microfoaming agent level detector, the memory is encoded with instruction that when executed performs the steps of determining a microfoaming agent supply amount by way of the microfoaming agent level detector, and communicating the microfoaming agent supply amount to a remote data processing resource or a computing device by way of the communication interface.

Additional shortcomings of the prior art are overcome and additional advantages are provided through the provision of a method of disinfecting a fluid transmission line. The method comprises the steps of initiating the flow of water into an aqueous ozone generator, generating an ozonated concentrate liquid by way of an electrochemical generator which comprises an ion exchange material. The electrochemical generator is integrated into the aqueous ozone generator. The electrochemical generator receives the water and generates from the water the ozonated concentrate liquid.

The method continues by generating the flow of a microfoaming ozonated liquid by ratiometrically mixing a microfoaming agent with the ozonated concentrate liquid and disinfecting a fluid transmission line by dispensing the microfoaming ozonated liquid through the fluid transmission line.

Additional shortcomings of the prior art are overcome and additional advantages are provided through the provision of a method of disinfecting a fluid transmission line. The method comprises the steps of inserting, in a removable manner, a cartridge into fluid communication with an aqueous ozone generator. The cartridge comprises a microfoaming agent, initiating the flow of water into the aqueous ozone generator, and generating an ozonated concentrate liquid by way of an electrochemical generator which comprises an ion exchange material. The electrochemical generator is integrated into the aqueous ozone generator. The electrochemical generator receives the water and generates the ozonated concentrate liquid.

The method continues by generating the flow of a microfoaming ozonated liquid by ratiometrically mixing the microfoaming agent with the ozonated concentrate liquid from the aqueous ozone generator and disinfecting a fluid transmission line by dispensing the microfoaming ozonated liquid through the fluid transmission line.

Additional shortcomings of the prior art are overcome and additional advantages are provided through the provision of a method of disinfecting a fluid transmission line. The method comprises the steps of initiating the flow of water into an aqueous ozone generator and generating an ozonated concentrate liquid by way of an electrochemical generator which comprises an ion exchange material. The electrochemical generator is integrated into the aqueous ozone generator. The electrochemical generator receives the water and generates from the water the ozonated concentrate liquid.

The method continues by generating the flow of a microfoaming ozonated liquid by ratiometrically mixing a microfoaming agent with the ozonated concentrate liquid and disinfecting a surface by dispensing the microfoaming ozonated liquid onto the surface.

The method continues by determining a microfoaming agent supply amount by way of the microfoaming agent level detector and communicating, by way of a control system, the microfoaming agent supply amount to a remote data processing resource or a computing device by way of a communication interface. The control system comprises the microfoaming agent level detector and the communication interface.

System and computer program products corresponding to the above-summarized methods are also described and claimed herein.

Additional features and advantages are realized through the techniques of the present invention. Other embodiments and aspects of the invention are described in detail herein and are considered a part of the claimed invention. For a better understanding of the invention with advantages and features, refer to the description and the drawings.

BRIEF DESCRIPTION OF THE FIGURES

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 1 illustrates one example of a microfoaming aqueous ozone system;

FIGS. 2-3 illustrates one example of using microfoaming aqueous ozone for cleaning and disinfecting fluid transmission lines;

FIG. 5 illustrated examples of microfoaming agent and ozonated concentrate liquid flow governors;

FIG. 6 illustrates one example of a microfoaming aqueous ozone system block diagram;

FIG. 7 illustrates one example of a system and network diagram;

Figure 3:
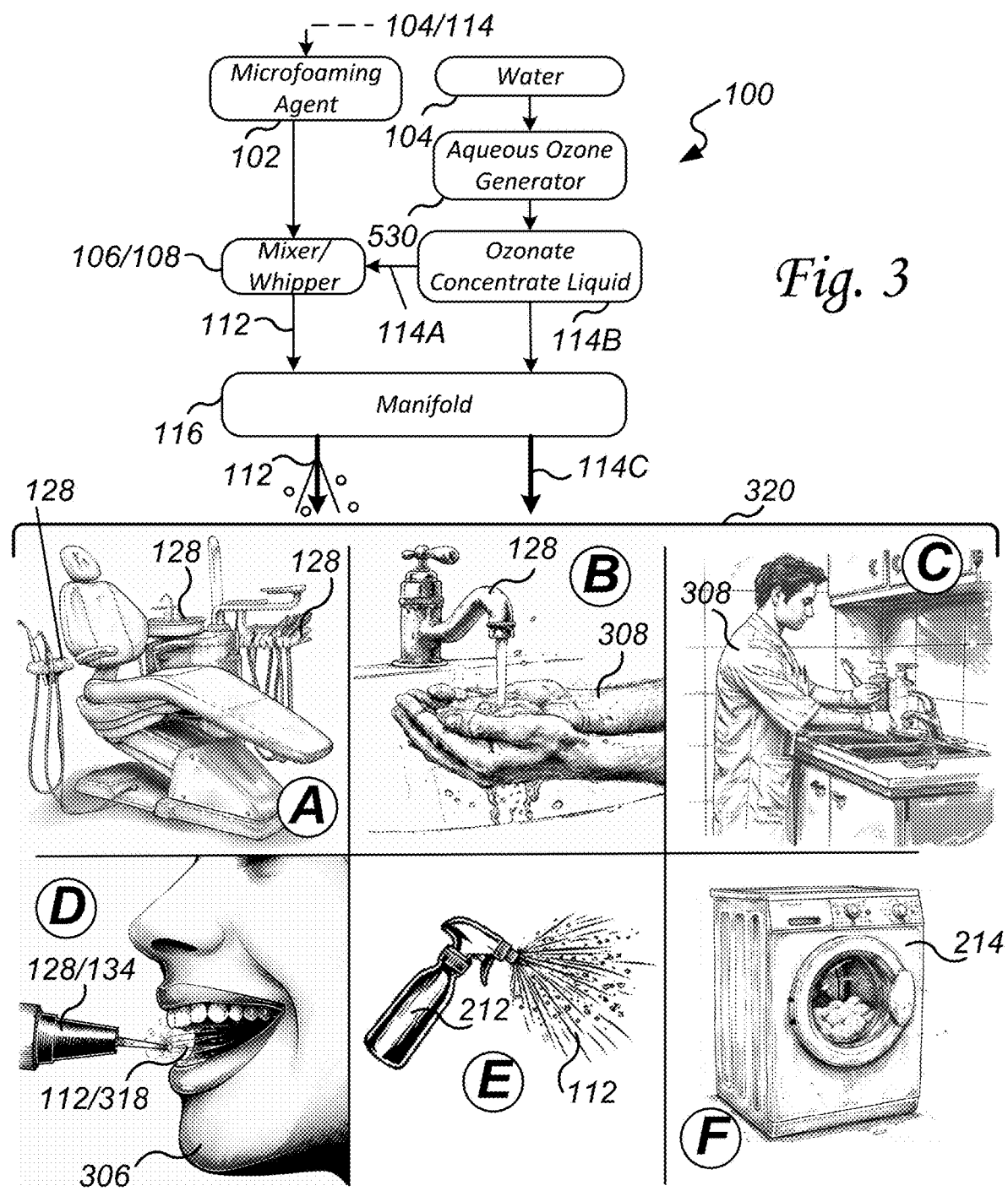

The detailed description explains the preferred embodiments of the invention, together with advantages and features, by way of example with reference to the drawings.

DETAILED DESCRIPTION OF THE INVENTION

Turning now to the drawings in greater detail, it will be seen that in FIG. 1 there is illustrated one example of a microfoaming aqueous ozone system 100.

An advantage, in the present invention, is that a microfoaming agent 102 can be combined with an ozonated contrate liquid 114 which is generated from an aqueous ozone generator 530 to form a microfoaming ozonated liquid 112. The microfoaming ozonated liquid 112 can be dispensed through fluid transmission lines 128 as well as dispensed on surfaces 312, providing superior cleaning and disinfection.

In operation, microfoamed aqueous ozonated solutions can offer several advantages over plain aqueous ozonated water when it comes to disinfection. Such advantages and benefits can include for example and not a limitation:

Increased contact time: Microfoaming the ozonated solution creates a larger surface area, allowing for better contact with fluid transmission line surfaces, surfaces in general, as well as in the oral cavity surfaces 318 of patients, including teeth, gums, and tongue. This increased contact time can enhance the effectiveness of ozone as a disinfectant;

Improved penetration: The microfoam can reach into crevices and hard-to-reach areas in fluid transmission lines, on surfaces, as well as in the mouth, ensuring more thorough disinfection compared to plain water, which may not have as much penetrating power;

Enhanced retention: Microfoam tends to adhere to surfaces better than liquid, which means the ozonated solution stays in contact with fluid transmission line surfaces, surfaces in general, as well as oral cavity tissues of patients for a longer period. This prolonged exposure can improve the disinfection process;

Mechanical action: The act of microfoaming can provide a mechanical action that aids in dislodging scale, contaminants, biofilms, and other substances. With regards to oral cavity 318 applications, such mechanical action can aid in dislodging food particles, plaque, and debris, further contributing to a cleaner and healthier mouth;

Improved taste and mouthfeel: Depending on the microfoaming agent used, in oral applications, the microfoam can have a pleasant taste and mouthfeel, making the disinfection process more comfortable and enjoyable for the person;

Reduced splatter: The use of microfoaming ozonated solutions can reduce splattering during the application, leading to a neater and more controlled disinfection procedure;

And other advantages and benefits.

In an exemplary embodiment, to create microfoam in aqueous ozonated water while maintaining safety and a pleasant mouthfeel (for oral cavity applications), food-grade foaming agents can be used that are safe for human consumption. Such foaming agents can include for example and not a limitation:

Organic foaming agents: Ingredients like organic soy lecithin or organic egg white powder can be used to create foam in water. These ingredients are generally safe for consumption and can provide a smooth and creamy mouthfeel;

Plant-based proteins: Ingredients like pea protein or oat protein can also be used to create foam in water. These proteins can add a creamy texture and are often used in dairy alternatives for their foaming properties;

Natural gums: Gums like xanthan gum or guar gum can be used as foaming agents in water. These gums are derived from natural sources and can create stable foam with a pleasant mouthfeel;

Coconut milk or cream: Adding a small amount of coconut milk or cream to aqueous ozonated water can create a frothy texture and add a hint of coconut flavor. Coconut-based ingredients are generally safe and can enhance the overall drinking experience;

Whipping siphon: Using a whipping siphon with nitrous oxide cartridges can also create foam in water. This method is often used in culinary applications to create airy textures and can be a fun way to experiment with foam in ozonated water;

And other types and/or kinds of, microfoaming agents, as may be required and/or desired in a particular embodiment.

It's important to use these ingredients in moderation and follow recommended guidelines for their usage to ensure safety and a pleasant taste. Additionally, consider the specific application and preferences of consumers when choosing a foaming agent for aqueous ozonated water.

An advantage, in the present invention, is that the use of microfoaming ozonated liquid in fluid transmission lines disinfection is human-safe should a portion of the fluid be ingested, whereas caustic chemical cleaning of tubes and pipes isn't human-safe and if ingested can make a person very sick. In addition, the mechanical action of the microfoam better dislodges biofilm contaminant and biofilm buildup resulting in a superior disinfection down to the surface of the fluid transmission line or surface, whereas non-foamed caustic solutions and other non-foamed solutions can pass over the biofilm without disloging or penetrating to the actual surface of the tube or pipe thus not achieving a total clean or disinfection.

With reference to FIG. 1, water 104 can be routed to an aqueous ozone generator 530 through suitable tubing, piping, or other methods. Such water 104 can be from a plumbed water source under pressure and governed to a desired flow rate as needed, pumped or gravity-fed from a tank or reservoir, or provided in other suitable ways. Additionally and selectively, a portion of the water 104 can be route 104A to mix with a portion of the microfoaming agent 102 if that is what is desired and/or required for proper microfoam creation.

In an exemplary embodiment, the aqueous ozone generator 530 generates from the water 104 an ozonated concentrate liquid 114. Additionally and selectively, a portion of the ozonated concentrate liquid 114 can be route 114A to mix with a portion of the microfoaming agent 102 if that is what is desired and/or required for proper microfoam creation.

The microfoaming agent can be routed by tubing, pipe, or other suitable methods to a mixer 106 that also receives the ozonated concentrate liquid 114. The mixer combines that microfoaming agent 102 ratiometrically with the ozonated concentrate liquid 114 creating a microfoaming ozonated liquid 112. Additionally, the mixer 106 functionality can also include a whipper 108 that can be configured to agitate the microfoaming ozonated liquid 112 to enhance foaming, and for other benefits.

In an exemplary embodiment, in operation, whipper 108 can receive and agitate some of the water 102 and the microfoaming agent 102, creating a microfoam that is blended with the ozonated concentrate liquid 114 to form the microfoaming ozonated liquid 112. Alternatively, the whipper 108 can receive and agitate some of the ozonated concentrate liquid 114 and the microfoaming agent 102, creating the microfoam that is blended with the ozonated concentrate liquid 114 to form the microfoaming ozonated liquid 112.

In an exemplary embodiment, a portion of water 104A or ozonated concentrate liquid 114A illustrated as dashed lines can selectively be routed as and if needed to the microfoaming agent 102 dosing location. In this regard, viscous microfoaming agents, powered microfoaming agents, or certain other types of microfoaming agents may need to be diluted or otherwise wetted to create a suitable flow through the system and/or for accurate dosing.

In an exemplary embodiment and as better illustrated in at least FIG. 2, the mixer 106 functionality can also include a manifold 116 that can be configured to selectively control the flow and mixing of several flow streams from a plurality of fluid transmission lines 128A. As an example and not a limitation, one input flow stream of the microfoaming ozonated liquid 112 can be split, by the manifold 116, and individually controlled on/off manually or by way of control system 500 into many individual streams of microfoaming ozonated liquid 114 through the plurality of fluid transmission lines 128B to be distributed to different endpoints and/or use applications. In another example, streams of water 104, ozonated concentrate liquid 114, microfoaming ozonated liquid 112, beverages, beverage syrups, foods like yogurt and others, beer, or other suitable fluids can be input into the manifold 116, and the output from the manifold 116 individually selected manually or by way of control system 500 for on/off flow through the manifold 116 to a destination point of use. the can be either of those liquids or a combination thereof. In this regard, one or more of the fluid transmission lines 128 can receive water 104, ozonated concentrate liquid 114, microfoaming ozonated liquid 112, food or beverage fluids such as beer, soda, yogurt, and other, other suitable fluids, or a combination thereof, as may be required and/or desired in a particular embodiment.

In applications of fluid transmission line cleaning and disinfection, the manifold 116 can switch temporarily from the food or beverage or other suitable fluid in the transmission line 128B to the microfoaming ozonated liquid 112, purging the transmission line 128B which can be a long-length 314 by opening the valve 316 to allow the microfoaming ozonated liquid 112 to traverse the fluid transmission line 128B and egress the valve 316. In this regard, the microfoaming ozonated liquid 112 contacts the entire interior surface of the length 314 of the fluid transmission line 128B as well as the valve 316 cleaning and disinfecting.

In an exemplary embodiment and with reference to FIG. 1, the microfoaming ozonated liquid 112 can be dispensed through fluid communication lines 128 and/or onto surfaces for surface disinfection applications 320 a few of which, for example, and not a limitation, can include in reference 'A' dental line cleaning and disinfection including in reference 'B' oral cavity 318 disinfection of patients 306 using dental sprayers 134 or other suitable fluid transmission lines 128 and devices, in reference 'C' food or beverage lines cleaning and disinfection such as beer taps 310 and valves 138, or other similar taps and/or valves, and reference 'D' surface 312 cleanings and disinfection by a user 308 using a spray nozzle 136 or other suitable devices.

For disclosure purposes, fluid transmission line 128 can include tubes, pipes, sprayers, spray bottles, faucets, valves, pumps, and other devices and lines. Such fluid transmission lines 128 can include food or beverage lines that carry beer, syrup concentrates, and other food or beverage fluids. Such fluid transmission lines 128 can include dental water lines commonly found in dental offices. Such dental water lines can include device and tool cleaning stations, hand washing sinks, and dental chair fluid supply lines typically for use with patients including tools, sprayers, spray bottles, sinks, faucets, valves, pumps, and other dental water line applications. Other fluid transmission lines 128 can include those associated with dispensing the microfoaming ozonated liquid 112 onto surfaces such as tables, counters, or other suitable surfaces, as may be required and/or desired in a particular embodiment.

In an exemplary embodiment, a microfoaming aqueous ozone disinfection system 100 can comprise an aqueous ozone generator 530 that receives water 104, a microfoaming agent 102, and an electrochemical generator 516 that comprises an ion exchange material 534. The electrochemical generator 516 can be integrated into the aqueous ozone generator 530. The electrochemical generator 530 is configured to receive water 104 and generate from the water 104 an ozonated concentrate liquid 114.

The microfoaming aqueous ozone disinfection system 100 can further comprise a mixer 106 that blends the microfoaming agent 104 with the ozonated concentrate liquid 114, creating a microfoaming ozonated liquid 112 that can dispensed for use in disinfecting one or more surfaces 130/312/318 including fluid transmission line 128 that comprises a surface 130 on the interior which is better illustrated in at least FIG. 6.

In an exemplary embodiment, the microfoam 102 portion of the microfoaming ozonated liquid 112 operates to increase ozonated concentrate liquid 114 contact time and mechanical action on the surface 130/312/318 agitating scale, contaminates, pathogens, or biofilm buildup on the surface, improving the ability of the ozonated concentrate liquid portion of the microfoaming ozonated liquid 112 to dislodge, penetrate, and disinfect the surface 130/312/318.

Referring to FIG. 2, illustrated one example of a microfoaming aqueous ozone system 100. In an exemplary embodiment, in many bars, restaurants, and other establishments a plurality of food or beverage containers 202 can be stored in a backroom or other suitable location, and dispensing nozzles or valves 318 are located in customer areas 204. In operation, lengthy 314 fluid transmission lines 128 can be used to interconnect food or beverage containers 202 in the backroom with valves 316 in customer area 202. Such long lengthy 134 fluid transmission lines 128 require frequent cleaning and disinfection. An advantage, in the present invention, is that the microfoaming ozonated liquid can periodically be flushed down the fluid transmission lines 128 to clean and disinfect the interior surface 130. The microfoam portion of the microfoaming ozonated liquid operates to increase ozonated concentrate liquid contact time on the surface and agitate scale, contaminates, pathogens, or biofilm buildup on the surface, improving the ability of the ozonated concentrate liquid portion of the microfoaming ozonated liquid to disinfect the surface.

Referring to FIG. 3, there is illustrated one example of a microfoaming aqueous ozone system 100. In an exemplary embodiment, fluid transmission line 128 can be dental water lines that run to points of use throughout a dentist's office. Such points of use can be, for example and not a limitation, in reference 'A' dental chairs, in reference 'B' sinks for hand washing and other purposes, in reference 'C' medical instrument washing and disinfection, in reference 'D' oral cavity dental 318 rinse for patients 306, in reference 'E' mobile spray bottles that are filled with microfoaming ozonated water 114 for disinfecting surfaces, in reference 'F' washing, and numerous other uses, as may be required and/or desired in a particular embodiment.

In an exemplary embodiment, the fluid transmission line 128 can be a food or beverage fluid transmission line, a dental water line, a wound treatment water line, a surgical water line, a washing machine water line, or other suitable type of lines, as may be required and/or desired in a particular embodiment.

In an exemplary embodiment, the microfoaming ozonated liquid 112 can be dispensed through the dental rinse nozzle 134 into the oral cavity 318 of a patient 306, wherein the oral cavity 318 of the patient is the surface.

In an exemplary embodiment, the dental rinse nozzle 134 can switch between dispensing, water 104, ozonated concentrate liquid 114, or microfoaming ozonated liquid 112, for maximum flexibility and patient treatment, as may be required and/or desired in a particular embodiment.

Figure 4:
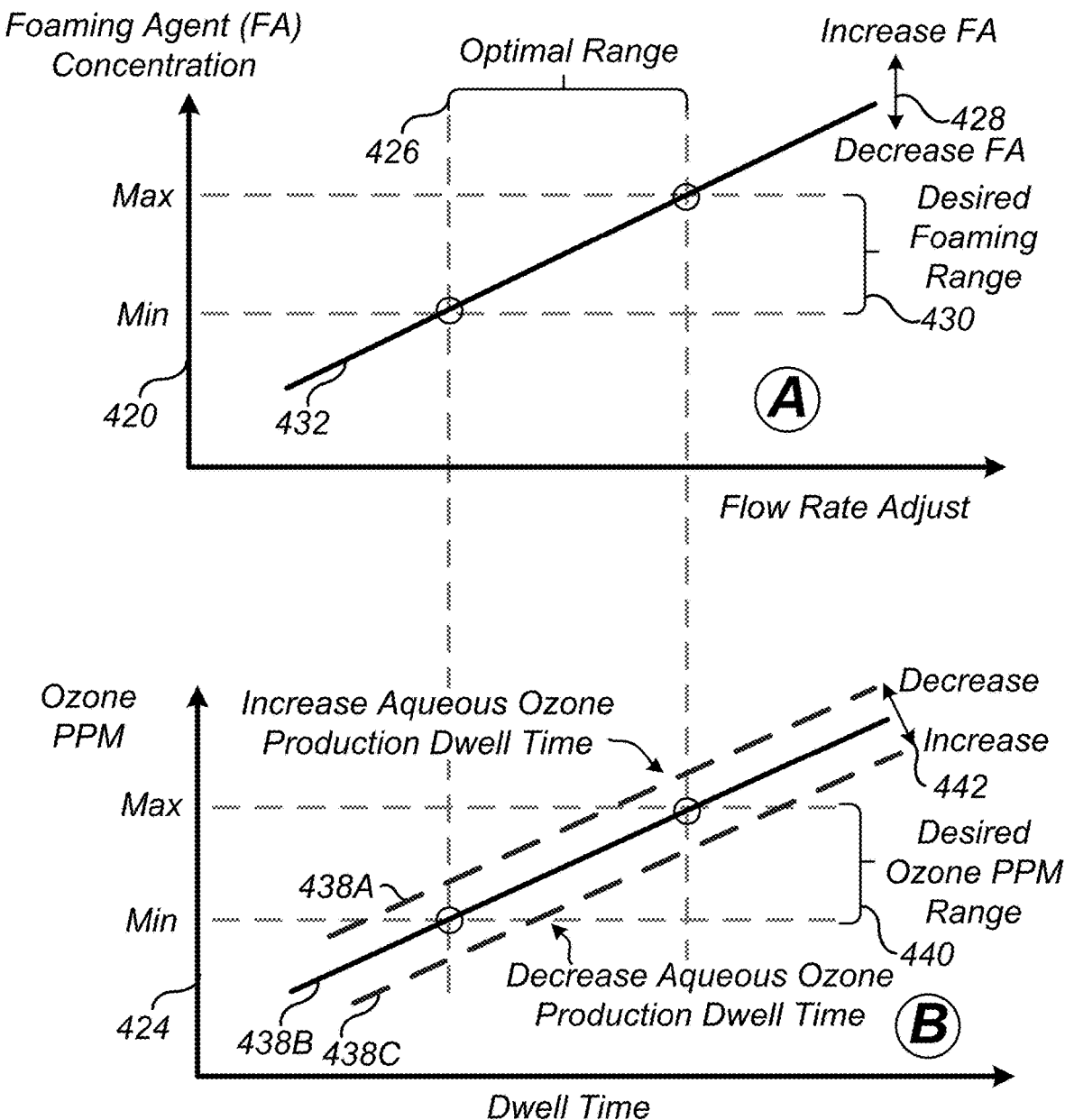
FIG. 4 illustrates one example of the relationship between foaming agent concentration and ozone concentration of the concentrated ozone liquid.

Referring to FIG. 4, there is illustrated one example of the relationship between foaming agent concentration 420 and ozone concentration of the concentrated ozone liquid 424. In an exemplary embodiment, there is an optimal range 426 between foaming agent concentration 420 and ozone concentration 424.

In reference 'A', the foaming agent concentration 420 can be adjusted to a desired foaming range 430 which is also within the optimal range 426 of the microfoaming ozonated water 112. In this regard, the microfoaming agent 102 dosing amount 432 can be increased or decreased 428 to obtain the desired foaming range 430 and stay within the optimal range 426. Such microfoaming agent 102 dosing and flow rate adjustment can be accomplished by way of flow governors 122/142/146.

In reference 'B', the desired ozone ppm range 440 of the ozonated concentrate liquid 114 is selected to achieve the desired disinfection level and/or desired log reduction. As an example and not a limitation, ozonated concentrate liquid 114 with a concentration level between a minimum 0.5 ppm and a maximum 1.5 ppm is often desired for surfaces 130/312/318 disinfection, though other concentrations can be selected, as may be required and or desired in a particular embodiment. To adjust the ozonated concentration 438A-C the water 104 flow rate can be adjusted 442. In this regard, decreasing the flow rate allows the electrochemical generator 516 to operate on each portion of the water 104 longer increasing 438A the aqueous ozone concentration. Conversely, increasing the flow rate of the water reduces the amount of time the electrochemical generator 516 has to operate on each portion of the water 104, decreasing 438C the aqueous ozone concentration.

The variable of ozone concentration can be controlled by adjusting the flow rate of the mixture 102/140 which adjusts the dwell time of the mixture passing through the aqueous ozone generator 530 including the electrochemical generator 516, in a continuous flow manner. Such can be controlled by modulating an orifice size either fixed, manual, or controlled by the control system 500 and associated pumps/valves/orifices.

Referring to FIG. 5, there are illustrated examples of microfoaming agent 102 and ozonated concentrate liquid 114 flow governors 122/142/146. In an exemplary embodiment, flow governors 122/142/146 can be used throughout the microfoaming aqueous ozone system 100 as needed to regulate the dosing and/or flow rate of the microfoaming agent 102, water 104, microfoaming ozonated liquid 112, ozonated concentrate liquid 114, or other fluids. In operation, the flow governors 122/142/146 control the amount of microfoaming agent 102 in the microfoaming ozonated liquid 112, the concentration of the ozonated concentrate liquid 114 by adjusting the dwell time of the water 104 in the aqueous ozone generator 530, or regulating other parameters of the system, as may be required and/or desired in a particular embodiment. Additionally, other types or kinds of suitable governors can be used, as may be required and/or desired in a particular embodiment.

In an exemplary embodiment, flow governors 122/142/146 can be used to regulate 432 the amount of microfoaming agent 102 dosed into the microfoaming ozonated liquid 112. In this regard, flow governors 122/142/146 can increase 428 the dosing amount of microfoaming agent 102 in the microfoaming ozonated liquid 112 and can decrease 428 the dosing amount to reduce the amount of microfoaming agent 102 in the microfoaming ozonated liquid 112, and may be required and/or desired in a particular embodiment.

In an exemplary embodiment, one or more microfoaming agent governors 122/142/146 regulate the amount of the microfoaming agent 102 in water 104, controlling a microfoaming level 432 of the microfoaming ozonated liquid 112 within a desired microfoaming range 430.

In an exemplary embodiment, goverrner 122 can be an electronic pump/valve/orifice control, that can automatically adjust the flow rate of the desired fluid 102/104/112/114 by way of control system 500. Flow governor 142 can be a fixed adjust washer style with a variable size orifice that adjusts the flow rate of the desired fluid 102/104/112/114. Flow governor 146 can be manually adjustable style allowing a technician 302 or other authorized persons to manually adjust the flow rate of the desired fluid 102/104/112/114. Additionally, the manually adjusted flow governor 146 can have a range indicator 220 and an adjust indicator 206 which is movable with respect to the range indicator 220 to indicate the position or flow rate setting of the governor 146.

In an exemplary embodiment and with reference to at least FIGS. 4 and 5, flow governors 122/142/146 can be used to modulate the water 104 flow rate into the aqueous ozone generator 530 to regulate 438A-C the dwell time to change the ozone parts per million (PPM) concentration amount of the ozonated concentrate liquid 112. In this regard, the water 104 flow rate can be decreased, increasing the aqueous ozone production dwell time 442 through the electrochemical generator 516 which increases the ozone concentration level of the ozonated concentrate liquid 112 to be within the desired ozone concentration range 440. Conversely, the water 104 flow rate can be increased to lower the ozonated concentration level by reducing the dwell time 442 of the water 104 within the aqueous ozone generator 530.

In an exemplary embodiment, one or more flow governors 122/142/146 regulate an aqueous ozone production dwell time of the ozonated concentrate liquid through the electrochemical generator 516, controlling an ozone concentration level 438B of the ozonated concentrate liquid 114 within a desired ozone concentration range 440.

In an exemplary embodiment, at least one fluid transmission line 128 can have an interior 130 that comprises the surface. The microfoaming ozonated liquid 114 is dispensed into and through the fluid transmission line 128 disinfecting the surface 130.

Referring to FIG. 6, there is illustrated one example of a control system 500 for the microfoaming aqueous ozone system 100. In an exemplary embodiment, control system 500 can be integrated into and control a microfoaming aqueous ozone system 100. In addition, control system 500 can be a web-enabled control system.

The term "web-enabled" or "web-enabled control system" or "web-enabled control system 500" in the present invention is intended to mean an Internet-of-things device. In this regard, a device that is capable of connecting a physical device such as a microfoaming aqueous ozone system 100 to the digital world. Stated differently, web-enabling is equipping a device with the necessary electronics to be monitored, and controlled, and data communicate locally and remotely with other data-communicating devices. Such other data-communicating devices can be smartphones, tablets, laptops, mobile communication devices, other web-enabled devices, remote data processing resources, servers, and similar devices.

In addition, and with reference to at least FIG. 7, such data communicating devices 732 can data communicate with remote data processing resources 702 and store and retrieve data from databases 706A-C, and other data processing resources, as may be required and/or desired in a particular embodiment. Laptops, smartphones, smartwatches, tablets, desktop computers, servers, mobile communication devices, and other types and kinds of data communication devices can all be data communicating devices 732 also referred to as computing devices 732.

In operation, a technician 302, an administrator 304, or other authorized people can use computing device 732 to interact with the aqueous ozone generator 530 or microfoaming aqueous ozone system. The aqueous ozone generator 530 can comprise the electrochemical generator 516 and ion exchange material 534.

In this regard, a technician 302 can be a person who operates, maintains, cleans, configures, repairs, or performs other functions on or with the aqueous ozone generator 530 or microfoaming aqueous ozone system 100. An administrator 304 can be a person who administers, provides remote service or technical support, or be other types or kinds of authorized user, as may be required and/or desired in a particular embodiment.

In operation the control system 500, by way of the communication interface 508 can data communicate with remote data processing resources 702. Such remote data processing resources 702 can be servers or other types or kinds of data processing resources. Furthermore, data communicating devices 732, remote data processing resources 702, data storage resources 706A-C, and other types and kinds of data communicating devices can data communicate over a global network 700. The Internet is a global network 700.

In an exemplary embodiment and with reference to at least FIG. 6, the microfoaming aqueous ozone system 100 can be equipped with a web-enabled control system 500. Such a web-enabled control system 500 can comprise a microcontroller 502 which is operationally related to a memory 504, a display 506, a plurality of communication interfaces 508, general purpose input and outputs (GPIO) 510, a plurality of sensors 512, a global position system (GPS) 514, an electrochemical generator 516 with an ion exchange material 534, a humidity sensor 518, a current sensor 520, a plurality of ozone sensors 522, an accelerometer 524, a power supply 526, a flow controller 528, an aqueous ozone generator 530, a TDS sensor 532, a water ($H_2O$) conductivity sensor 536, and a microfoam agent level detector 538.

The microcontroller 502 can be INTEL, ZILOG, MICROCHIP, AMD, ARM, and/or other types or kinds of microcontrollers.

The memory 504 can be a combination of random access memory (RAM), read only memory (ROM), flash, hard drives, solid-state drives, USB flash drives, and/or other types and kinds of memory.

The display 506 can be a liquid crystal display (LCD), organic light emitting diode (OLED), or light emitting diode (LED), as well as have touch input capabilities and/or other types and kinds of displays and user inputs as may be required and/or desired in a particular embodiment.

The communication interface 508 can be LAN, WAN, USB, Ethernet, RS232, RS485, serial, WiFi, 802.11abgn and similar, second-generation (2G), third-generation (3G), fourth-generation (4G), or fifth-generation (5G) compatible, Bluetooth, TCP, UDP, Mesh Network, Zigbee, Pico Network, LORAN, and/or other types and kinds of communication interfaces and protocols.

In an exemplary embodiment, the communication interface 508 is operationally related to the microcontroller 502. The control system 500, by way of the communication interface 508, data communicates with the remote data processing resource 702, data communication devices 732, and other data processing resources in a local area network environment or a wide area network environment across a global network 700 in a wired or wireless manner as may be required and/or desired in a particular embodiment. The Internet is a global network 700.

The GPIO 510 can be transistor-to-transistor (TTL), complementary metal-oxide-semiconductor (CMOS), transistors, buffers, relays, pushbuttons, switches, and/or other types and kinds of GPIO circuits.

The sensors 512 and/motion sensor 518 can be passive infrared (PIR) motion sensors, infrared, thermal, Doppler radar, ultrasonic, capacitance, touch-type, optical, Hall effect, switch, fingerprint, and other types of biometric sensors, and/or other types and kinds of sensors. Additionally, sensor 512 can be ambient condition sensors such as temperature, moisture, humidity, sunlight, and/or other types and kinds of sensors.

In an exemplary embodiment, analog-type sensor determinations can be converted to digital values so that the microcontroller 502 can process the data. Alternatively, the microcontroller 502 can perform analog-to-digital conversions if equipped to perform such functions.

The global positioning system (GPS) 514 can be used to track the location of the microfoaming aqueous ozone system 100, and data communicates by way of the communication interface 508 to remote data processing resources 702. In operation, reports, maps, and other information can then be used to inform the motion of and or location of the microfoaming aqueous ozone system 100.

The electrochemical generator 516 can be an electrolysis-based device that utilizes ion exchange material 534 and other devices and processes to produce chemical compounds from water such as ozone $O_3$.

The humidity sensor 518 can be utilized to determine the surrounding environment 202 humidity level.

The current sensor 520 can be configured to measure the supply electrical current to the electrochemical generator 516, the aqueous ozone generator 530, a combination 516/530 thereof, and/or other devices and systems, as may be required and/or desired in a particular embodiment.

The ozone sensor 522 can be configured to monitor the ozone concentration supplied to the system or other sources of ozonated liquid, as may be required and/or desired in a particular embodiment.

The accelerometer 524 can be configured to monitor the motion systems and devices, as required and/or desired in a particular embodiment.

The power supply 526 can be AC, DC, battery, solar, and/or other types and kinds of power supplies.

The flow controller 528 can be used to control a plurality of pumps/valves/orifice controls 120. Such flow controller 528 and the plurality of pumps/valves/orifice controls 120 can be actuated and/or controlled by way of relays, metal-oxide-semiconductor field-effect transistors (MOSFET), or other types and kinds of controlling devices.

The aqueous ozone generator 530 receives water as an input and uses the electrochemical generator 516 which is integrated into the aqueous ozone generator 530 to produce high concentrations of aqueous ozone molecules. Such concentrations of aqueous ozone can range from 1 ppm to 10 ppm or other desired range, as may be required and/or desired in a particular embodiment.

The total dissolved solids (TDS) sensor 532 can be a conductivity-based sensor or other types or kinds of TDS sensor, as may be required and/or desired in a particular embodiment.

The water conductivity sensor 536 can be a contacting, inductive, or other types or kinds of sensors, as may be required and/or desired in a particular embodiment.

The microfoam agent level detector 538 can be configured to monitor and determine the amount of the microfoam agent 102 remaining for use. The microfoam agent 102 is a consumable in the system 100 that periodically needs replenishment. In this regard, in an exemplary embodiment, when the microfoam agent level detector indicates replenishment of the microfoam agent 102 is desirable the cartridge 140 that comprises the microfoam agent 102 can be replaced by a technician 302.

The microfoam agent level detector 538 can be contacting or switch style, optical, weight, inductive, capacitive, or other types or kinds of sensors, as may be required and/or desired in a particular embodiment.

In an exemplary embodiment, a user interface for the microfoaming aqueous ozone system 100 can comprise at least one of the following a display 506, a display 506 with touchscreen, a communication interface 508 configured to data communicate with a remote data processing resource 702 such as a server 702 and/or a computing device 732.

The user interface for the microfoaming aqueous ozone system 100 can further comprise a plurality of button input capabilities by way of the GPIO 510, or other user interfaces. The user interface is operationally related to the microcontroller 502.

Referring to FIG. 7, there is illustrated one example of a system and network diagram. In an exemplary embodiment, users of the platform and network can include technicians 302, administrators 304, or other authorized persons.

Each of the users uses computing devices 732A-C to data communicate over a global communication network 700 with one or more data processing resources 702. The computing devices 732A-C can be laptop computers, desktop computers, smartphones, tablets, or other types and kinds of computing devices, as may be required and/or desired in a particular embodiment. For disclosure purposes, computing devices 732A-C can be referred to as computing devices 732. Additionally, laptop and desktop types of computing devices 732 can be referred to as computing devices 712C, computing devices 732 such as smartphones can be referred to as computing devices 732B, and computing devices 732 such as tablets can be referred to as computing devices 732A. In operation, any of the users can use any of the types of computing devices 732A-C, without limitation to the type or kind of computing device 732, as may be required and/or desired in a particular embodiment. The global communication network 700 can be the Internet.

The computing devices 732 can comprise a microprocessor 704B/704C, a database 706B/706C, memory 708B/708C, a communication interface 710B/710C, a display 712B/712C, and a plurality of general-purpose inputs and outputs (GPIO) 714B/714C.

Additionally, mobile type of computing device 732A/732B (tablets, smartphones, and others) can comprise a global positioning system (GPS) 716, and a microphone and/or camera 718.

In general, computing devices 232 can be configured with other functions and features, as may be required and/or desired in a particular embodiment.

In an exemplary embodiment, the microprocessor 704B is operationally related to database 706B, memory 708B, communication interface 710B, display 712B, and GPIO 714B.

In an exemplary embodiment, the microprocessor 704C is operationally related to database 706C, memory 708C, communication interface 710C, display 712C, GPIO 714C, and if equipped, with GPS 716, and microphone and/or camera 718. The computing devices 732 each rely on a suitable power source 720B/720C which can include a rechargeable battery, external power supply, or other types and/or kinds of power sources.

Microprocessor 704B/704C can be INTEL, ZILOG, MICROCHIP, AMD, ARM, and/or other types or kinds of microprocessors.

Database 706B/706C can be SQL, MYSQL, MARIADB, ORACLE, MS ACCESS, network-accessible storage, flat files, a combination thereof, or other types and kinds of databases.

Memory 708B/708C can be a combination of RAM, ROM, flash, hard drives, solid-state drives, USB flash drives, micro-SD cards, or other types of removable memory, and/or other types and kinds of memory.

The communication interfaces 710B/710C can be local area network (LAN), wide area network (WAN), universal serial bus (USB), Ethernet, RS232, RS485, serial, Wi-Fi, 802.11abgn and similar, 2G 3G 4G 5G compatible, Bluetooth, transmission control protocol (TCP), user datagram protocol (UDP), Mesh Network, Zigbee, Pico Network, long-range navigation (LORAN), and/or other types and kinds of communication interfaces and protocols.

Display 712B/712C can be a liquid crystal display (LCD), light emitting diode (LED), organic light emitting diode (OLED), or other types and kinds of displays.

The general-purpose inputs and outputs (GPIO) 714B/714C can be TTL, CMOS, MOSFET, transistors, buffers, relays, pushbuttons, switches, and/or other types and kinds of GPIO circuits. In an exemplary embodiment, some of the GPIO 214 lines can be used to drive a touch screen input, biometric input devices, keyboards, and/or types and kinds of computing device input devices.

Global positioning system (GPS) device 716 can be used to determine the geographic location of technician 302 and others who are carrying a computing device 732 equipped with a GPS 716. In this regard, such computing devices 732 are typically mobile computing devices such as tablets 732A, smartphones 732B, and other similar types and/or kinds of mobile computing devices 732.

Microphone and/or camera 718 can be used to record audio, and video, and take pictures. In this regard, users 304/306 can use their computing devices equipped with a microphone and/or camera 718 to make digital media records that can be selectively shared as appropriate including on social media and other digital media outlet locations.

With reference to at least FIG. 7, the data processing resource 702 can be a server, network storage device, or other types and kinds of data processing resources. Such data processing resources can be AMAZON WEB SERVICES (AWS), MICROSOFT AZURE, or other types and kinds of hosted data processing resource services. For disclosure purposes, a remote data processing resource 702 can also be referred to as server 702.

The data processing resource 702 can comprise a microprocessor 704A, a database 706A, memory 708A, and a communication interface 710A. The microprocessor 704A is operationally related to database 706A, memory 708A, and communication interface 710A.

The microprocessor 704A can be INTEL, ZILOG, MICROCHIP, AMD, ARM, and/or other types or kinds of microprocessors.

The database 706A can be SQL, MYSQL, MARIADB, ORACLE, MS ACCESS, network accessible storage, flat files, a combination thereof, or other types and kinds of databases.

The memory 708A can be a combination of RAM, ROM, flash, hard drives, solid-state drives, USB flash drives, micro-SD cards, or other types of removable memory, and/or other types and kinds of memory.

The communication interfaces 710A can be LAN, WAN, USB, Ethernet, RS232, RS485, serial, Wi-Fi, 802.11abgn and similar, 2G 3G 4G 5G compatible, Bluetooth, TCP, UDP, Mesh Network, Zigbee, Pico Network, LORAN, and/or other types and kinds of communication interfaces and protocols.

Figure 8:
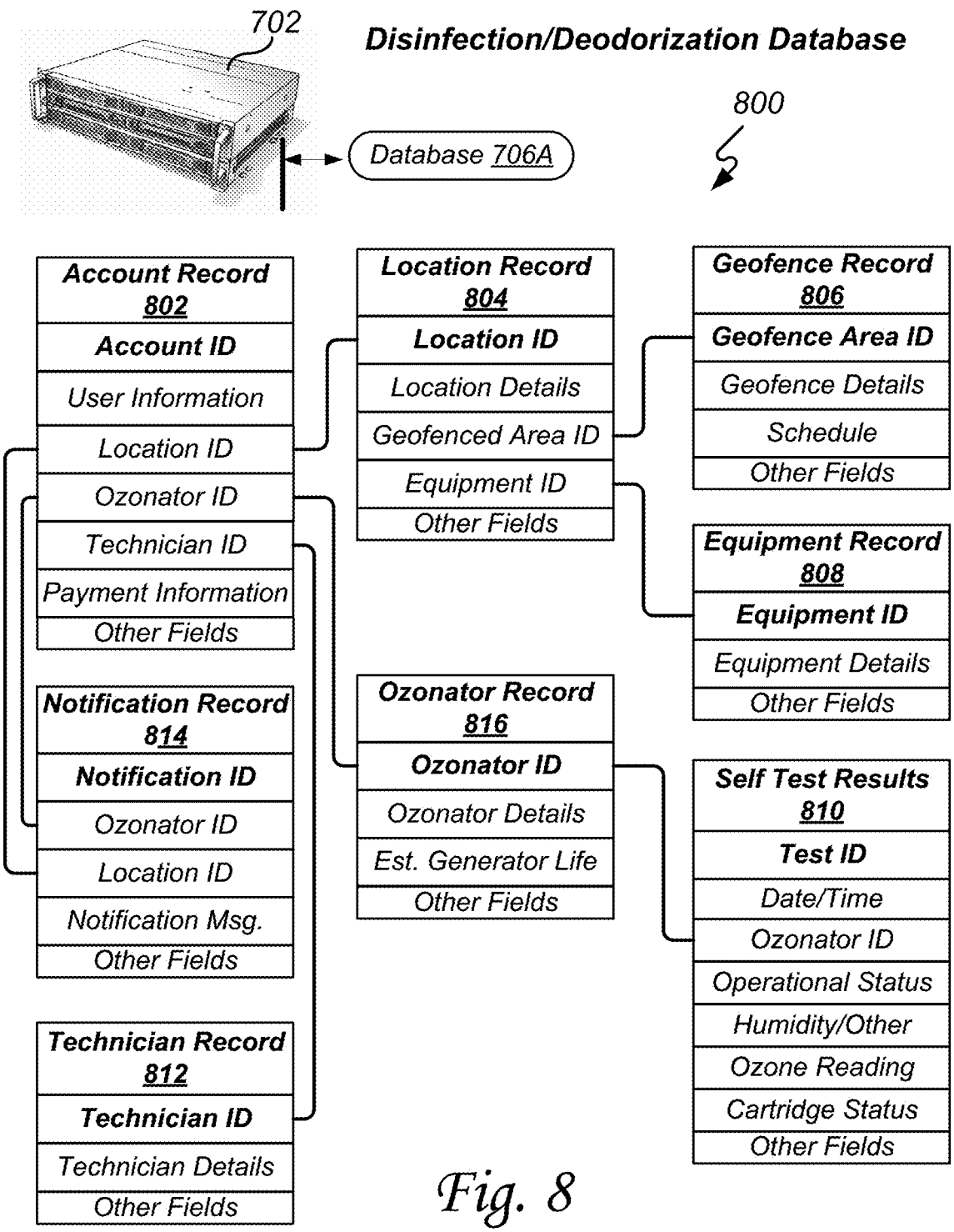
FIG. 8 illustrates one example of an ozone disinfection database structure.

Referring to FIG. 8, there is illustrated one example of an ozone disinfection/deodorization database structure 800. In an exemplary embodiment, at least one database 706A/706B/706C can be implemented on at least one of the data processing resources 702 also referred to as server 702, or computing devices 732. In operation, one or more databases 706A/706B/706C can be accessed/created/managed/maintained as appropriate by more than one stakeholder. In this regard, in addition to system administrators and other authorized persons, other stakeholders can access/create/manage/maintain as appropriate.

In an exemplary embodiment, such databases 706A/706B/706C can be SQL, MYSQL, MARIADB, ORACLE, MS ACCESS, network-accessible storage, flat files, a combination thereof, or other types and kinds of databases.

In an exemplary embodiment, the ozone disinfection/deodorization database 900 can reside on a remote data processing resource 702 in database 706A. In this regard, the ozone disinfection/deodorization database 900 can comprise a series of tables, records, fields, and accounts that include account record 802, location record 804, geofence record 806, equipment record 808, self-test results 810, technician record 812, notification record 814, ozonator record 816, and/or other types or kinds of records as may be required and/or desired in a particular embodiment. The database structure illustrated in FIG. 8 also illustrates certain of the relationships between the various tables.

In an exemplary embodiment, the data structure is illustrative and can be expanded and modified without particular limitation as needed and as appropriate to support the functionality and methods of the present invention and to support future functionality and methods of the present invention as it grows and evolves over time without any particular limitations.

Figure 9:
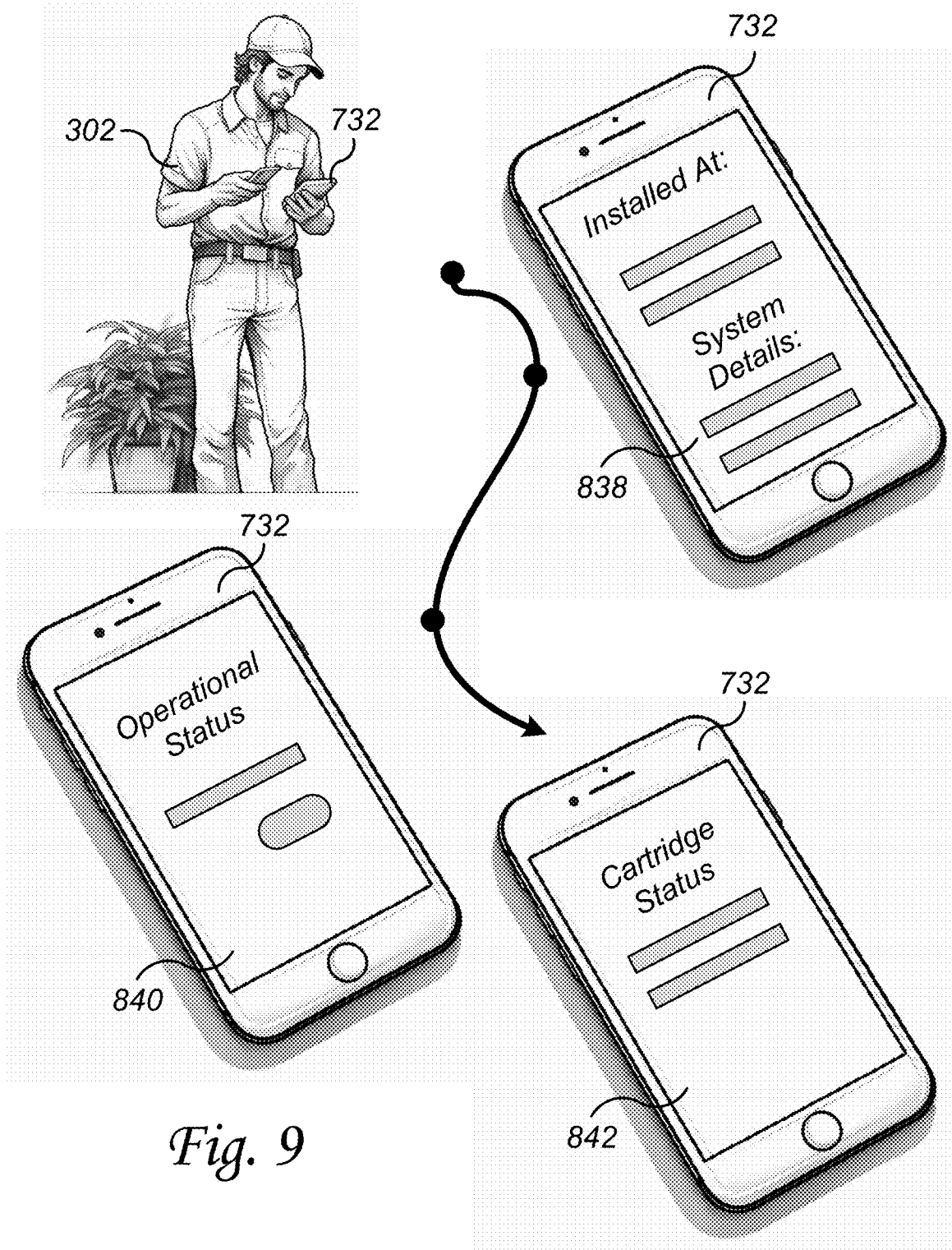
FIG. 9 illustrates one example of a technician's use of a software application.

Referring to FIG. 9, a technician's use of a software application. In an exemplary embodiment, a software application or website can be used in combination with the computing device 732A/B to identify the microfoaming aqueous ozone system 100, view operational statuses, record the test results and other results, and see other useful data by way of data communicating with a remote data processing resource 702. In some embodiments, certain microfoaming aqueous ozone system 100 may have the ability to data communicate 734 directly with a remote data processing resource 702, eliminating the need for computing device 732A/B to act as an intermediary device to record test results on the remote data processing resource 702.

In an exemplary embodiment, a computing device 732, operated by technician 302, data communicates with a remote data processing resource 702, and receives from the remote data processing resource 702, by way of the computing device 732 a plurality of microfoaming aqueous ozone system 100 location 838 and service life data 840 that corresponds to the remaining service life the electrochemical generator 516, the microfoaming agent 102 cartridge 842, and other service life information, as may be required and/or desired in a particular embodiment.

Figure 10:
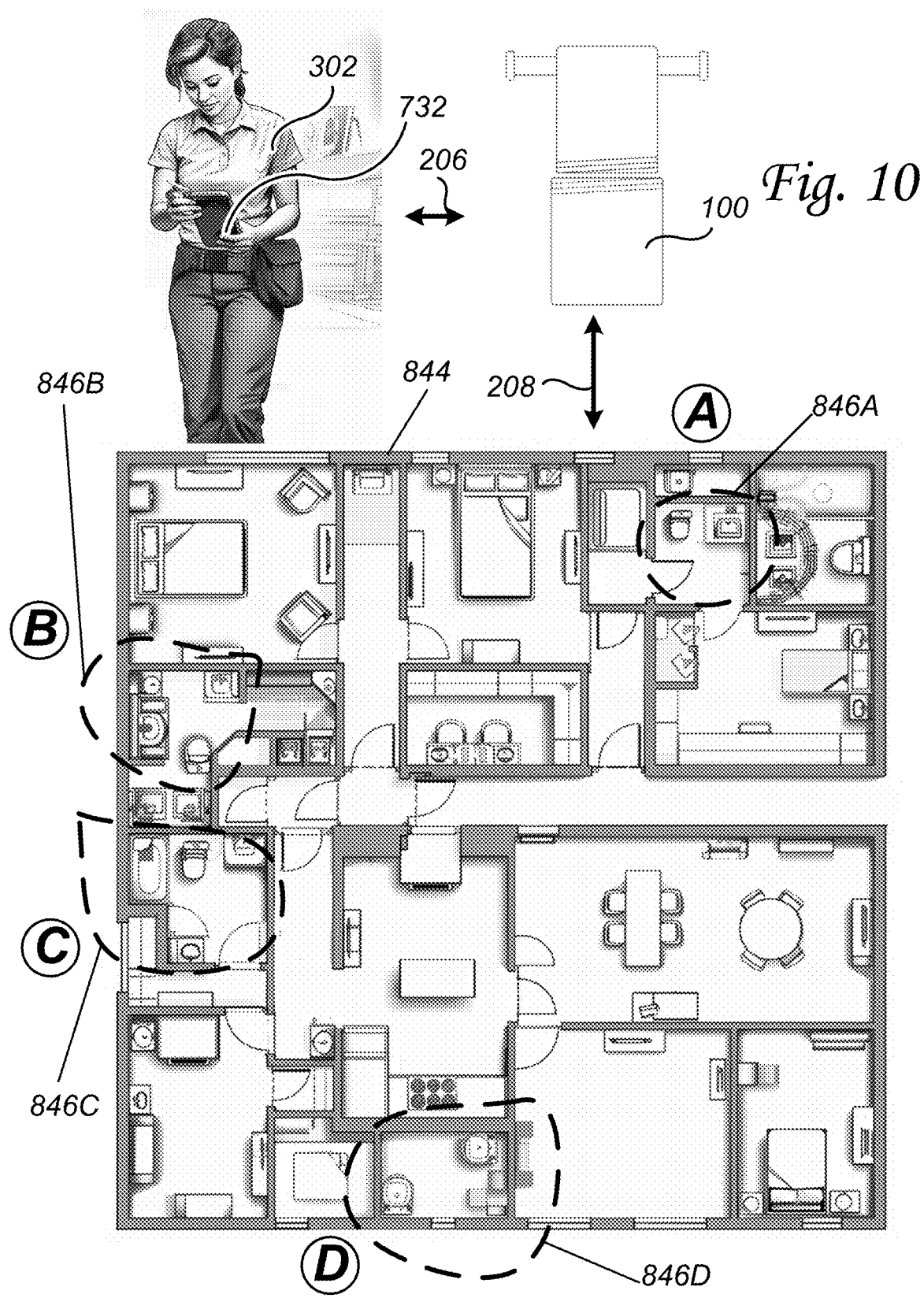
FIGS. 10-12 illustrate examples of a method of disinfecting a fluid transmission line.

Referring to FIG. 10, there is illustrated one example of a floor plan 844 to monitor geofenced or geolocate room spaces 'A' 846A, 'B' 846B, 'C' 846C, and 'D' 846D that have installed 208 a microfoaming aqueous ozone system 100. In an exemplary embodiment, technician 302, by way of computing platform 732, can data communicate with server 732 or data communicate 206 with individual microfoaming aqueous ozone sys 100 to ascertain operational status and location within a floor plan area 844.

Figure 11:
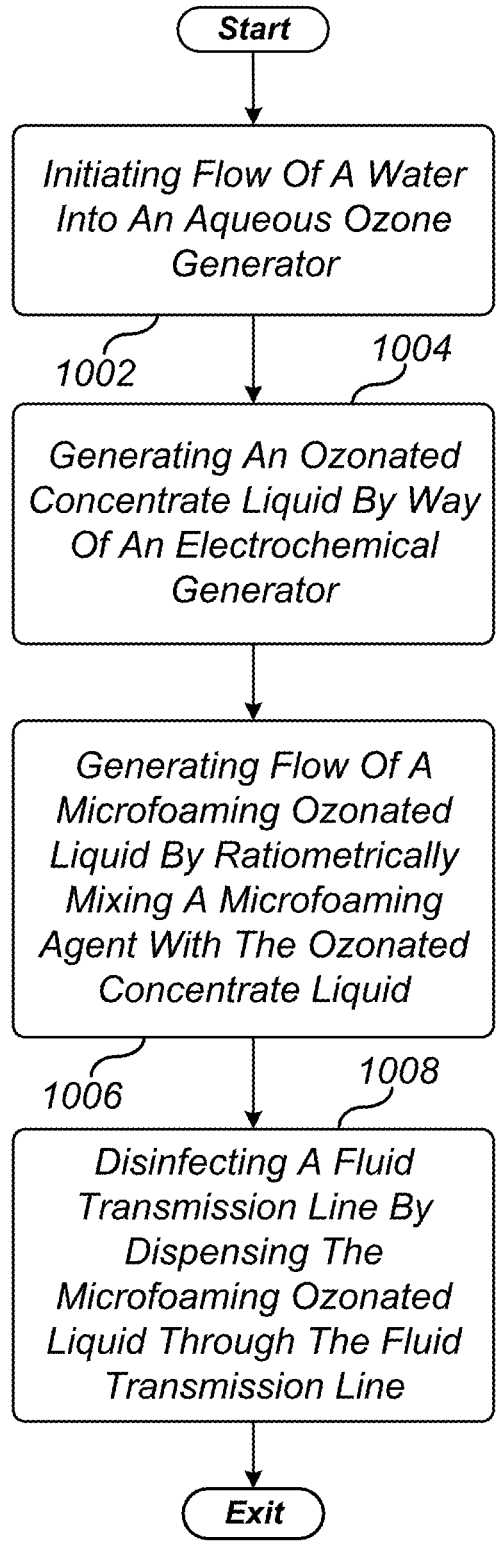

Referring to FIG. 11, there is illustrated one example of a method of disinfecting a fluid transmission line 128. In an exemplary embodiment, the method begins in step 1002 by initiating the flow of water 104 into an aqueous ozone generator 530, and in step 1004 by generating an ozonated concentrate liquid 114 by way of an electrochemical generator 516 which comprises an ion exchange material 534. The electrochemical generator 516 can be integrated into the aqueous ozone generator 530. The electrochemical generator 516 receives the water 104 and generates from the water 104 the ozonated concentrate liquid 114.

The method continues in step 1006 by generating the flow of a microfoaming ozonated liquid 112 by ratiometrically mixing a microfoaming agent 102 with the ozonated concentrate liquid 114, and in step 1008 by disinfecting a fluid transmission line 128 by dispensing the microfoaming ozonated liquid 112 through the fluid transmission line 128. The method is then exited.

Figure 12:
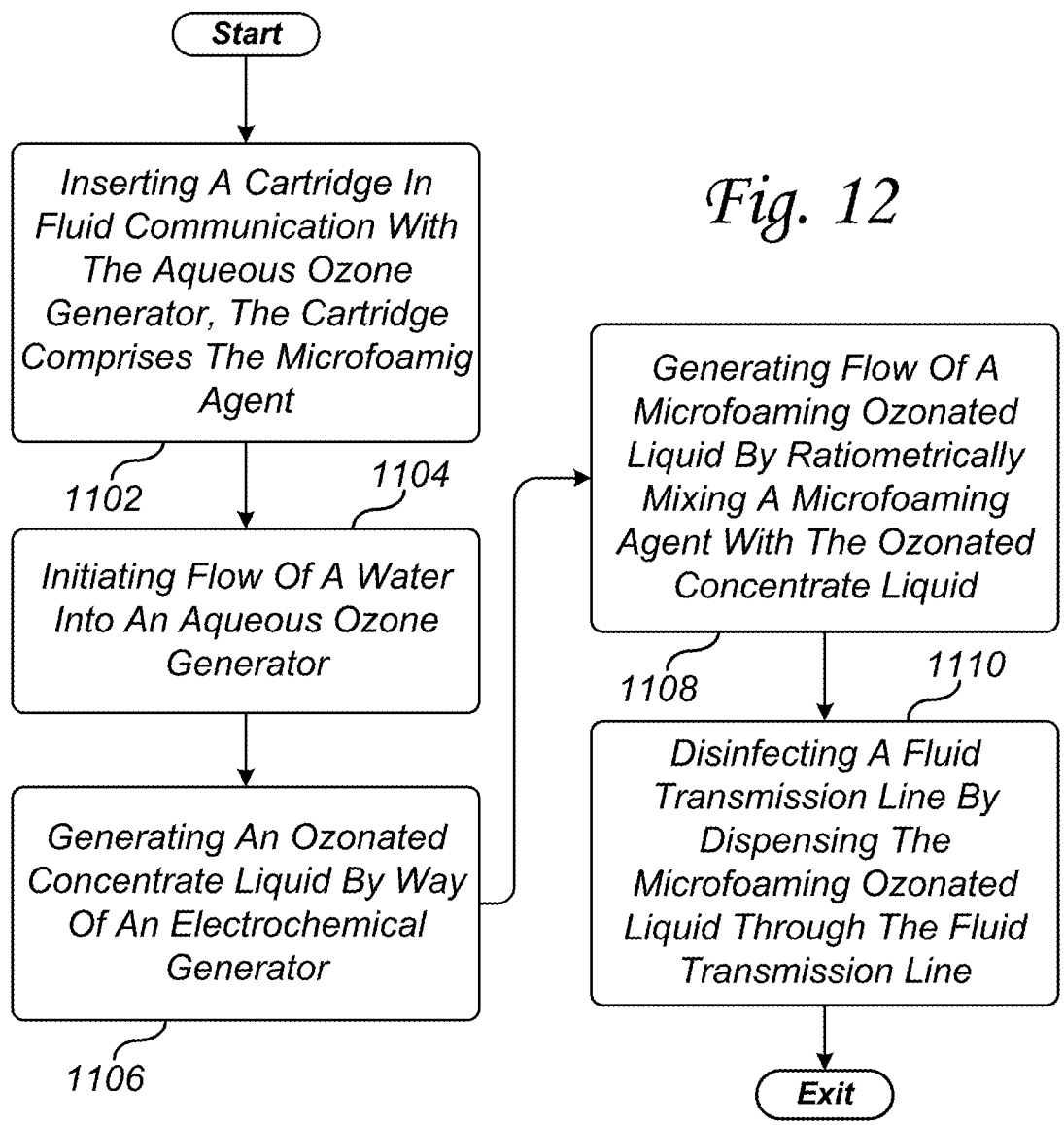

Referring to FIG. 12, there is illustrated one example of a method of disinfecting a fluid transmission line 128. In an exemplary embodiment, the method begins in step 1102 by inserting 350, in a removable manner, a cartridge 140 into fluid communication with an aqueous ozone generator 530. The cartridge 140 comprises a microfoaming agent 102, and in step 1004 by initiating the flow of water 104 into the aqueous ozone generator 530.

The method continues in step 1106 by generating an ozonated concentrate liquid 114 by way of an electrochemical generator 516 which comprises an ion exchange material 534. The electrochemical generator 516 can be integrated into the aqueous ozone generator 530. The electrochemical generator 516 receives water 104 and generates from the water 104 the ozonated concentrate liquid 114.

The method continues in step 1108 by generating the flow of a microfoaming ozonated liquid 112 by ratiometrically mixing the microfoaming agent 102 with the ozonated concentrate liquid 114, and in step 1110 by disinfecting a fluid transmission line 128 by dispensing the microfoaming ozonated liquid 112 through the fluid transmission line 128. The method is then exited.

Figure 13:
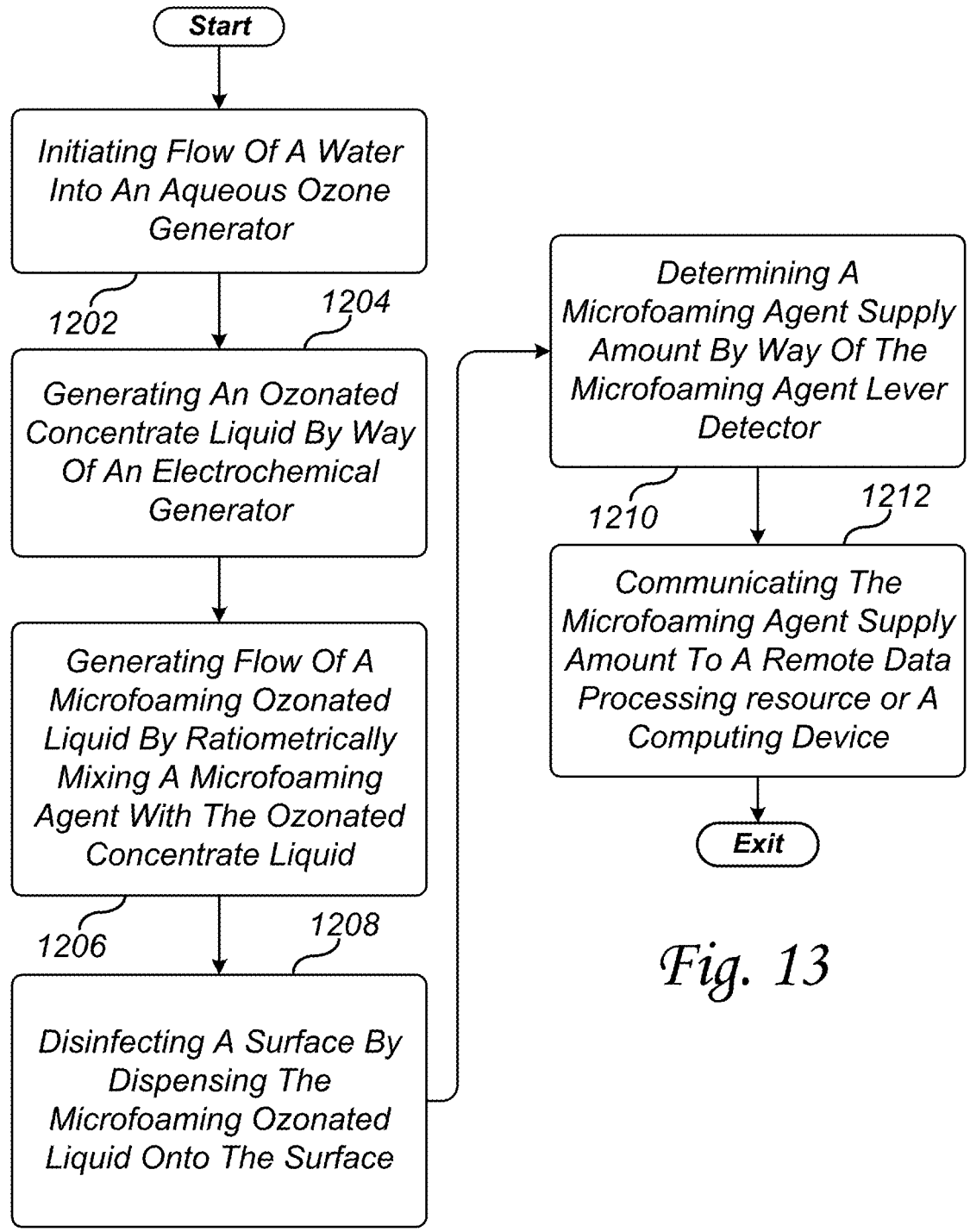
FIGS. 13-15 illustrate exemplary embodiments that can be used interchangeably with the methods of the present invention.

Referring to FIG. 13, there is illustrated one example of a method of disinfecting a fluid transmission line 128. In an exemplary embodiment, the method begins in step 1202 by initiating the flow of water 104 into an aqueous ozone generator 530, and in step 1204 by generating an ozonated concentrate liquid 114 by way of an electrochemical generator 516 which comprises an ion exchange material 534. The electrochemical generator 516 can be integrated into the aqueous ozone generator 530. The electrochemical generator 516 receives the water 104 and generates from the water the ozonated concentrate liquid 114.

The method continues in step 1206 by generating the flow of a microfoaming ozonated liquid 112 by ratiometrically mixing a microfoaming agent 102 with the ozonated concentrate liquid 114, and in step 1208 by disinfecting surface 130/312/318 by dispensing the microfoaming ozonated liquid 112 onto the surface.

The method continues in step 1210 by determining a microfoaming agent supply amount by way of the microfoaming agent level detector 538, and in step 1212 by communicating data, by way of a control system 500, the microfoaming agent supply amount to a remote data processing resource 702 or a computing device 732 by way of a communication interface 508. The control system 500 comprises the microfoaming agent level detector 538 and the communication interface 508. The method is then exited.

Figure 14:
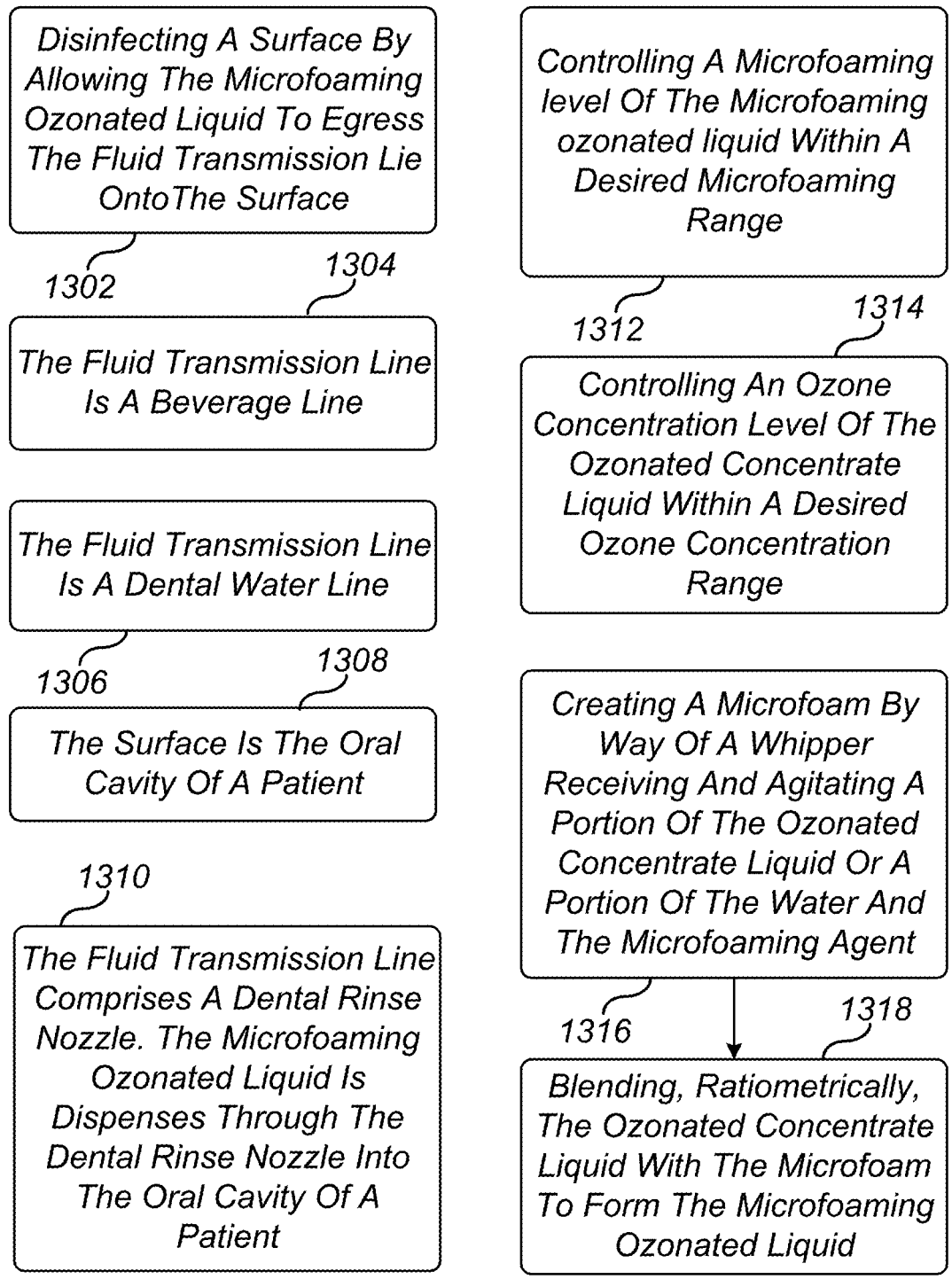

Referring to FIG. 14, there are illustrated exemplary embodiments that can be used interchangeably with the methods of the present invention.

In step 1302, disinfecting surface 312 by allowing the microfoaming ozonated liquid 112 to egress the fluid transmission line 128 onto surface 312.

In step 1304, the fluid transmission line 128 can be a food or beverage line. In an exemplary embodiment, such a food or beverage line can transfer beer, soda/syrup, yogurt, or other fluids from a backroom in a bar, restaurant, or other places to a point of dispense or other destinations, as may be required and/or desired in a particular embodiment.

In step 1306, the fluid transmission line 128 can be a dental water line. In an exemplary embodiment, dental water lines are typically used in dentist offices for hand washing/sinks, at the dental chair on patients for rinses and other purposes, for dental tool cleaning, and other applications and locations. In general, the water lines that run carry water for use in the dentist's office can be cleaned and disinfected with the present invention. In addition, the benefits of oral cavity 318 clean and rinse of patient 306 can be effectuated by allowing the microfoaming ozonated liquid 112 to egress a fluid transmission line 128/dental water line by way of a spray nozzle 134 into the patient's oral cavity 318.

In step 1308, the surface 318 is the oral cavity of patient 306. In an exemplary embodiment, the microfoaming ozonated liquid 112 can be flodded around the oral cavity 318 of patient 306 wherein the foam effectuates and enhances the ability of the ozonated concentrate liquid to disinfect the patient's oral cavity 318.

In step 1310, the fluid transmission line 128 comprises a dental rinse nozzle 134. The microfoaming ozonated liquid 112 can be dispensed through the dental rinse nozzle 134 into the oral cavity 318 of patient 306.

In step 1312, controlling a microfoaming level of the microfoaming ozonated liquid 114 within a desired microfoaming range by way of a microfoaming agent governor 1122/142/144/146/148 that regulates the amount of the microfoaming agent 102 in water 104 or ozonated concentrate liquid 114.

In step 1314, controlling an ozone concentration level of the ozonated concentrate liquid 114 within a desired ozone concentration range by way of a flow governor 120/142/146 that regulates an aqueous ozone production dwell time of the ozonated concentrate liquid through the electrochemical generator 516.

In step 1316, creating a microfoam by way of a whipper 108 receiving and agitating a portion of water 104 and the microfoaming agent 102, and in step 1318, blending, ratiometrically, the ozonated concentrate liquid 114 with the microfoam to form the microfoaming ozonated liquid 112.

Figure 15:
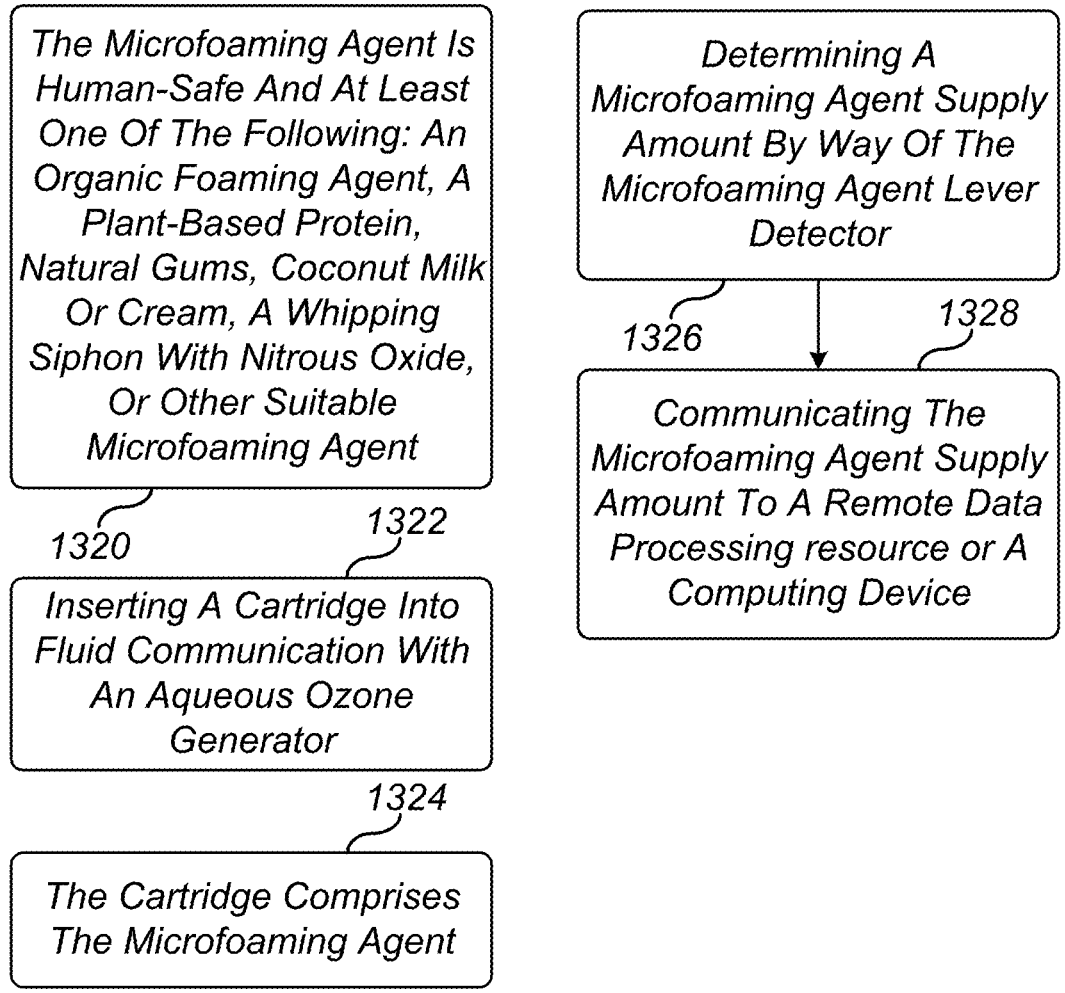

Referring to FIG. 15, there are illustrated exemplary embodiments that can be used interchangeably with the methods of the present invention.

In step 1320, the microfoaming agent 102 is human-safe and at least one of the following: an organic foaming agent, a plant-based protein, natural gums, coconut milk or cream, a whipping siphon with nitrous oxide, or other suitable microfoaming agents 102, a may be required and/or desired in a particular embodiment.

In step 1322, inserting 350, in a removable manner, cartridge 140 into fluid communication with an aqueous ozone generator, and in step 1324, cartridge 140 comprises a microfoaming agent.

In step 1326, determining a microfoaming agent supply amount by way of the microfoaming agent level detector 538, and in step 1328, communicating, by way of the control system 500, the microfoaming agent supply amount to a remote data processing resource 702 or a computing device 732 by way of the communication interface 508. The control system 500 comprises the communication interface 508 and the microfoaming agent level detector 538.

The capabilities of the present invention can be implemented in software, firmware, hardware, or some combination thereof.

As one example, one or more aspects of the present invention can be included in an article of manufacture (e.g., one or more computer program products) having, for instance, computer usable media. The media has embodied therein, for instance, computer readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

While the preferred embodiment of the invention has been described, it will be understood that those skilled in the art, both now and in the future, may make various improvements and enhancements which fall within the scope of the claims which follow. These claims should be construed to maintain the proper protection for the invention first described.

What is claimed is:

1. A disinfection system comprising:
   an aqueous ozone generator that creates an ozonated concentrate liquid from water;
   a whipper that receives a portion of the water and agitates the water and a microfoaming agent, creating a microfoam; and
   a mixer that blends the microfoam with the ozonated concentrate liquid to produce a microfoaming ozonated liquid.

2. The disinfection system in accordance with claim 1, further comprising:
   an electrochemical generator that comprises an ion exchange material, the electrochemical generator is integrated into the aqueous ozone generator, the electrochemical generator receives the water and generates from the water the ozonated concentrate liquid.

3. The disinfection system in accordance with claim 1, further comprising:
  one or more microfoaming agent governors configured to regulate the amount of the microfoaming agent in the water to control a microfoaming level of the microfoaming ozonated liquid within a desired microfoaming range.

4. The disinfection system in accordance with claim 2, further comprising:
  one or more flow governors configured to regulate an aqueous ozone production dwell time of the ozonated concentrate liquid through the electrochemical generator to control an ozone concentration level of the ozonated concentrate liquid within a desired ozone concentration range.

5. The disinfection system in accordance with claim 1, further comprising:
  a cartridge that inserts into fluid communication with the aqueous ozone generator, in a removable manner, the cartridge comprises the microfoaming agent.

6. The disinfection system in accordance with claim 1, further comprising:
  a fluid transmission line, the microfoaming ozonated liquid is dispensed into and through the fluid transmission line disinfecting the fluid transmission line.

7. The disinfection system in accordance with claim 6, wherein the fluid transmission line is a food or beverage fluid transmission line, a dental water line, a wound treatment water line, a surgical water line, or a washing machine water line.

8. The disinfection system in accordance with claim 1, further comprises:
  a dental rinse nozzle, the microfoaming ozonated liquid is dispensed through the dental rinse nozzle into the oral cavity of a patient, wherein the oral cavity of the patient is disinfected.

9. The disinfection system in accordance with claim 1, wherein the microfoaming agent is human-safe and at least one of the following: an organic foaming agent, a plant-based protein, natural gums, coconut milk or cream, or a whipping siphon with nitrous oxide.

10. A method of using the disinfection system of claim 1, the method comprising the steps of:
  creating the ozonated concentrate liquid from water by processing the water through the aqueous ozone generator configured to achieve a predetermined ozone concentration level;
  creating the microfoaming ozonated liquid by mixing a precisely metered amount of the microfoaming agent with the ozonated concentrate liquid to achieve a desired microfoaming consistency; and
  applying the microfoaming ozonated liquid as a disinfectant by dispensing it onto a target surface or into a fluid transmission line to enhance disinfection through increased contact time and surface penetration.

11. The method in accordance with claim 10, further comprising the steps of:
  initiating flow of the water into the aqueous ozone generator;
  generating flow of the microfoaming ozonated liquid by ratiometrically mixing the microfoaming agent with the ozonated concentrate liquid from the aqueous ozone generator; and
  disinfecting a dental rinse nozzle and an oral cavity of a patient by dispensing the microfoaming ozonated liquid through the dental rinse nozzle and into the oral cavity of the patient.

12. The method in accordance with claim 10, further comprising the steps of:
  initiating flow of the water into the aqueous ozone generator;
  generating flow of the microfoaming ozonated liquid by ratiometrically mixing the microfoaming agent with the ozonated concentrate liquid from the aqueous ozone generator; and
  disinfecting the fluid transmission line by dispensing the microfoaming ozonated liquid into and through the fluid transmission line.

13. A disinfection system comprising:
  an aqueous ozone generator that creates an ozonated concentrate liquid from water;
  a cartridge that inserts into fluid communication with the aqueous ozone generator, in a removable manner, the cartridge comprises a microfoaming agent; and
  a mixer that blends the microfoaming agent with the ozonated concentrate liquid, creating a microfoaming ozonated liquid.

14. The disinfection system in accordance with claim 13, further comprising:
  an electrochemical generator that comprises an ion exchange material, the electrochemical generator is integrated into the aqueous ozone generator, the electrochemical generator receives the water and generates from the water the ozonated concentrate liquid.

15. The disinfection system in accordance with claim 13, further comprising:
  a fluid transmission line, the microfoaming ozonated liquid is dispensed into and through the fluid transmission line disinfecting the fluid transmission line.

16. The disinfection system in accordance with claim 13, further comprising:
  a dental rinse nozzle, the microfoaming ozonated liquid is dispensed through the dental rinse nozzle into the oral cavity of a patient, wherein the oral cavity of the patient is disinfected.

17. A disinfection system comprising:
  an aqueous ozone generator that creates an ozonated concentrate liquid from water;
  a mixer that blends a microfoaming agent with the ozonated concentrate liquid from water creating a microfoaming ozonated liquid; and
  a control system comprises a microcontroller, a memory, a communication interface, and a microfoaming agent level detector, the microcontroller is operationally related to the memory, the communication interface, and the microfoaming agent level detector, the memory is encoded with instruction that when executed perform the steps of:
    determining a microfoaming agent supply amount by way of the microfoaming agent level detector; and
    communicating the microfoaming agent supply amount to a remote data processing resource or a computing device by way of the communication interface.

18. The disinfection system in accordance with claim 17, further comprising:
  an electrochemical generator that comprises an ion exchange material, the electrochemical generator is integrated into the aqueous ozone generator, the electrochemical generator receives the water and generates from the water the ozonated concentrate liquid.

19. The disinfection system in accordance with claim 17, further comprising:

at least one of a fluid transmission line, the microfoaming ozonated concentrate liquid is dispensed into and through the fluid transmission line disinfecting the fluid transmission line.

20. The disinfection system in accordance with claim 17, further comprising:
a dental rinse nozzle, the microfoaming ozonated liquid is dispensed through the dental rinse nozzle into the oral cavity of a patient, wherein the oral cavity of the patient is disinfected.

* * * * *